US008156158B2

(12) United States Patent
Rolls et al.

(10) Patent No.: US 8,156,158 B2
(45) Date of Patent: Apr. 10, 2012

(54) METHOD AND SYSTEM FOR USE OF A DATABASE OF PERSONAL DATA RECORDS

(75) Inventors: Dan Rolls, Rehovot (IL); Ilan Cohn, Herzliya (IL); Iphtach Cohen, Atlit (IL)

(73) Assignee: Famillion Ltd., Road Town, Tortola (VG)

( * ) Notice: Subject to any disclaimer, the term of this patent is extended or adjusted under 35 U.S.C. 154(b) by 81 days.

(21) Appl. No.: 12/669,765

(22) PCT Filed: Jul. 18, 2007

(86) PCT No.: PCT/IL2007/000909
§ 371 (c)(1),
(2), (4) Date: Jul. 12, 2010

(87) PCT Pub. No.: WO2009/010948
PCT Pub. Date: Jan. 22, 2009

(65) Prior Publication Data
US 2010/0287213 A1 Nov. 11, 2010

(51) Int. Cl.
G06F 17/30 (2006.01)
(52) U.S. Cl. ........................................ 707/803; 707/809
(58) Field of Classification Search .................... 707/803
See application file for complete search history.

(56) References Cited

U.S. PATENT DOCUMENTS

| 5,220,501 | A * | 6/1993 | Lawlor et al. ................... 705/40 |
| 5,857,028 | A | 1/1999 | Frieling |
| 6,175,831 | B1 | 1/2001 | Weinreich et al. |
| 6,373,488 | B1 | 4/2002 | Gasper et al. |
| 6,416,325 | B2 | 7/2002 | Gross |
| 6,513,059 | B1 | 1/2003 | Gupta et al. |
| 6,553,350 | B2 | 4/2003 | Carter |
| 6,570,567 | B1 | 5/2003 | Eaton |
| 6,704,787 | B1 | 3/2004 | Umbreit |
| 6,742,001 | B2 | 5/2004 | Ripley |
| 6,886,015 | B2 | 4/2005 | Notargiacomo et al. |
| 7,047,204 | B1 | 5/2006 | Wood et al. |
| 7,860,318 | B2 | 12/2010 | Mandelbaum et al. |
| 2001/0027671 | A1 | 10/2001 | Davis |

(Continued)

OTHER PUBLICATIONS

The Search Report issued Apr. 18, 2008 in International Application No. PCT/IL2007/000909.

*Primary Examiner* — Don Wong
*Assistant Examiner* — Binh V Ho
(74) *Attorney, Agent, or Firm* — The Nath Law Group; Susanne M. Hopkins; William L. Klima

(57) ABSTRACT

A system and method are presented for managing and using (e.g. for commercial or medical use) of a database. A verified database of a plurality of identified individuals is provided. The verified database comprises a plurality of individual-identifier data sets (IDSs) and relationship data. The verified database is processed in accordance with one or more parameters or conditions selected in accordance with at least one medical application, and a sub-group database is created including data records of the individuals from the verified database having said one or more selected parameters or conditions. This allows collection of data comprising the one or more selected parameters or conditions and delivery of at least part of the collected data to one or more users, and enables applying data from the verified database to provide personalized medicine service to at least one of the identified individuals.

23 Claims, 20 Drawing Sheets

U.S. PATENT DOCUMENTS

| | | |
|---|---|---|
| 2001/0037451 A1 | 11/2001 | Bhagavatula et al. |
| 2002/0048755 A1 | 4/2002 | Cohen |
| 2002/0049806 A1* | 4/2002 | Gatz et al. .................... 709/203 |
| 2002/0095357 A1* | 7/2002 | Hunter et al. .................. 705/27 |
| 2002/0143578 A1* | 10/2002 | Cole et al. ......................... 705/2 |
| 2003/0115459 A1 | 6/2003 | Monk |
| 2003/0126092 A1 | 7/2003 | Chihara |
| 2003/0154194 A1 | 8/2003 | Jonas |
| 2003/0182621 A1 | 9/2003 | Mazza et al. |
| 2003/0220980 A1 | 11/2003 | Crane |
| 2004/0010472 A1 | 1/2004 | Hilby et al. |
| 2005/0022239 A1* | 1/2005 | Meuleman ...................... 725/46 |
| 2005/0171832 A1 | 8/2005 | Hull et al. |
| 2005/0246314 A1* | 11/2005 | Eder ................................ 707/1 |
| 2006/0173792 A1 | 8/2006 | Glass |
| 2007/0005601 A1* | 1/2007 | Gaucas ............................. 707/9 |
| 2007/0005750 A1 | 1/2007 | Lunt et al. |
| 2007/0033203 A1 | 2/2007 | Nemazi et al. |
| 2007/0087365 A1 | 4/2007 | Van Criekinge et al. |
| 2007/0143625 A1 | 6/2007 | Jung et al. |

* cited by examiner

| PARAMETER | DATA ON A IN IDBs-A | | DATA ON A IN IDBs-B | | ACCEPT | SCORE (1-10) |
|---|---|---|---|---|---|---|
| AGE | 37 | A1 | 38 | | NO | 9 |
| GENDER | FEMALE | A2 | FEMALE | B2 | YES | 10 |
| PLACE OF BIRTH | BALTIMORE | A3 | NEW YORK | | NO | 4 |
| COLOR OF EYES | BLUE | A4 | BLUE | B4 | YES | 10 |
| DATE OF BIRTH | JANUARY, 11, 1969 | A5 | JANUARY, 11, 1969 | B5 | YES | 10 |
| FATHER's NAME | PETER | A6 | PETER | B6 | YES | 10 |
| MOTHER's NAME | MARY | A7 | MARIE | | NO | 8 |
| BROTHER's NAME | FRANK | A8 | | B6 | NO | 5 |
| RESIDENCE | NEW YORK | A9 | | | NO | 5 |

FIG. 5

METHOD AND SYSTEM FOR USE OF A DATABASE OF PERSONAL DATA RECORDS

FIELD OF THE INVENTION

The present invention concerns the construction of a database of individuals and various applications thereof. In particular, the present invention concerns the use of a database of individuals in personalized medicine based on authenticated medical and other personal data.

BACKGROUND OF THE INVENTION

The Internet is very useful as a medium of communication and provision and retrieval of information. The Internet became also a medium in which individuals form or associate themselves with virtual communities consisting of individuals with common interests, backgrounds, etc. In order to belong to such a virtual community an individual 'surfing' the Internet typically needs to locate the proper website and register. It would have been useful to have an Internet-based means that will be able to associate an individual with one or more communities ("community" including individuals with family relations, individuals having a common interest, individuals having a similar origin or background, etc.), based on a self entered profile.

The Internet also proved to be a useful tool for individuals to locate family members, lost friends, etc. This requires posting notes on appropriate virtual bulleting boards, using appropriate search engines, etc. This, however, is a relatively chance process and does not always bring the desired results. It would have been useful to streamline this process.

Some background information may be found in the following publications:

U.S. Pat. No. 6,373,488 to Gasper et al., discloses a three-dimensional tree-structured data display;

U.S. Pat. No. 6,416,325 to Gross discloses a genealogical analysis tool;

U.S. Pat. No. 6,513,059 to Gupta et al., discloses an adaptive collaborative intelligent network system;

U.S. Pat. No. 6,553,350 to Carter discloses a method and apparatus for pricing products in multi-level product and organizational groups;

U.S. Pat. No. 6,570,567 to Eaton, discloses a system and method for using a graphical interface for the presentation of genealogical information;

U.S. Pat. No. 6,742,001 to Ripley discloses a system and method for sharing data between hierarchical databases; and U.S. Pat. No. 6,886,015 to Notargiacomo et al., discloses a method and system for building a family tree.

Over the last decade, as the human genome has become unraveled, there has been a marked interest in developing systems and methods for providing personalized medicine services. "Personalized medicine" is understood to broadly pertain to providing a medical service to an individual, matched to his genetic makeup and to providing a tailored medical treatment at the right time, and at the right dosage based on his/her personalized medical parameters.

US 2002048755A, to Cohen, describes a system for developing diagnostic assays, useful in determining whether a particular therapeutic agent will benefit an individual, comprises a continuum of processes that advance diagnostic development while concomitantly benefiting development of the therapeutic agent. This continuum of processes, which is of dual use, in promoting both diagnostic and drug development, is highly economic and efficient, and creates synergy between pharmaceutical and diagnostic companies.

US 2005246314A, to Eder, describes methods, program storage devices and systems for developing a Personalized Medicine Service for an individual or group of individuals that can support the operation, customization and coordination of computer systems, software, products, services, data, entities and/or devices.

US 2007087365A, to Sieben et al., shows that there are twenty-three markers which are epigenetically silenced in ovarian cancers. The markers can be used diagnostically, prognostically, therapeutically, and for selecting treatments that are well tailored for an individual patient. Restoration of expression of silenced genes can be useful therapeutically, for example, if the silenced gene is a tumor-suppressor gene. Restoration can be accomplished by supplying non-methylated copies of the silenced genes or polynucleotides encoding their encoded products. Alternatively, restoration can be accomplished using chemical demethylating agents or methylation inhibitors. Kits for testing for epigenetic silencing can be used in the context of diagnostics, prognostics, or for selecting "personalized medicine" treatments.

GENERAL DESCRIPTION OF THE INVENTION

There is a need in the art in a novel technique enabling verification of personalized data and keeping it up-to-date in real-time, enabling to provide for example personalized medicine technique based on up-to-date authenticated personal records.

A serious issue with Internet use is the fact that it is difficult to verify the identity of communicating individuals. This relative difficulty in verifying an identity of surfing individuals is an issue in carrying out transactions, such as the purchase of goods or services, over the Internet. The difficulty in verifying identities of 'surfing' individuals is also a serious issue when confronting a certain individual who identifies himself to be someone other than he really is. Abuse of this nature is a serious issue in Internet chat rooms, in dating services and in many other cases.

The present invention provides a novel method and system for use of a database of authenticated identified individuals. In accordance with the invention a computerized system is provided that permits users of a computer network, particularly, but not exclusively, the Internet, to input data on themselves and related individuals and based on that, optionally with verification of data input by other individuals, a database of individuals, users and non-users, and their relationships is constructed. The method and system of the invention have a variety of different commercial utilities as will be elucidated by the different aspects and embodiments described below.

Thus, according to one broad aspect of the invention, there is provided a method for using and managing a database, the method comprising: providing a verified database of a plurality of identified individuals, the verified database comprising a plurality of individual-identifier data sets (IDSs) and relationship data; and processing said verified database in accordance with one or more selected parameters and creating a sub-group database including data records of the individuals from the verified database having said one or more selected parameters or conditions, thereby allowing collection of data characterized by the one or more selected parameters or conditions and delivery of at least part of the collected data to one or more users.

The verified database may be provided as follows: A plurality of individuals are permitted to enter individual-associated data bits (IDBs) into a computerized system, where each of the IDBs comprises at least one personal identifier relating to the individual and relationship data comprising data on one or more related individuals and the nature of relationship. The entered IDBs are processed to generate the IDS, one for each identified individual, being either the same individual who has entered the individual-associated data bits or one of the related individuals. Then, the verified database comprising IDSs of identified individuals is constructed.

In some embodiments of the invention, the processing of the verified database in accordance with one or more selected parameters or conditions is initiated by a request from a user. The user initiating a request may or may not be the individual whose data is included in the verified database. For example, such user may be constituted by a certain company requesting services from the system of the present invention, to collect data from and/or deliver certain information to the individuals included in the sub-group database.

According to some embodiments of the invention, the processing of the verified database comprises generating a request to at least some of the individuals whose data is included into the verified database to provide additional data according to the one or more selected parameters or conditions. This additional data may be used for updating the verified database, so as to construct the sub-group database from the updated verified database.

The one or more parameters may be selected according to one of the following applications: a commercial application, sectorial and targeted marketing application, a statistical application, an identifying application selected from identifying a hostile person, a lost person, a relationship between a deceased person and living person, a family application.

According to another broad aspect of the invention, there is provided a method for managing and using a database of identified individuals, the method comprising: (a) permitting a plurality of users to enter individual-associated data bits (IDBs) into a computerized system, each of the IDBs comprising at least one personal identifier relating to the user and relationship data comprising data on one or more related individuals and the nature of relationship; (b) processing the entered IDBs to generate an individual-identifier data set (IDS), one for each identified individual, being either one of the users or one of the related individuals and construct a verified database comprising IDSs of identified individuals; and (c) processing information in said verified database in accordance with one or parameters or condition selected for at least one commercial application.

According to some embodiments of the invention the processing results may be used for creating a medical database of at least some of the identified individuals. Such medical database may comprise information pertaining to at least one of a disease, a medical condition, a genotype, a phenotype, a family relationship; and a geographic location of at least one of the identified individuals. The commercial application may be based upon personalized medicine.

Thus, according to yet further aspect of the invention, there is provided a method for using and managing a database, the method comprising:
 providing a verified database of a plurality of identified individuals, the verified database comprising a plurality of individual-identifier data sets (IDSs) and relationship data; and
 processing said verified database in accordance with one or more parameters or conditions selected in accordance with at least one medical application and creating a sub-group database including data records of the individuals from the verified database having said one or more selected parameters or conditions, thereby allowing collection of data comprising one or more selected parameters or conditions and delivery of at least part of the collected data to one or more users and enable to apply data from said verified database to provide personalized medicine service to at least one of said identified individuals.

The selected parameters or conditions, in addition to said parameter(s) or condition(s) selected in accordance with at least one medical application, may include at least one parameter or condition selected according to one of the following applications: a commercial application, sectorial and targeted marketing application, a statistical application, an identifying application selected from identifying a hostile person, a lost person, a relationship between a deceased person and living person, a family application.

The processing of the verified database may comprise creation of a medical database of at least some of the identified individuals. Such medical database may comprise information pertaining to at least one of a disease, a medical condition, a genotype, a phenotype, a family relationship; and a geographic location of at least one of said identified individuals.

In some embodiments of the invention, the medical application is based upon personalized medicine. At least one personal medical record may be combined with data from the verified database. The personalized medicine service may be selected from a personalized treatment service, a personalized prevention service and a personalized prediction service.

According to yet another broad aspect of the invention, there is provided a computerized system for managing and using a database over a computer network, the system comprising a server system linked to the network and accessible by users via their communication devices connectable to the network, said server system comprising a processor utility, which is associated with a verified database of a plurality of identified individuals comprising a plurality of individual-identifier data sets (IDSs) and relationship data and which is adapted to carry out the following: process said verified database in accordance with one or more parameters or conditions selected according to at least one medical application and create a sub-group database comprising data about at least some of the identified individuals characterized by said one or more selected parameters or conditions, and apply data from said verified database in order to provide a personalized medicine service to at least one of said identified individuals.

The processor utility may be configured to be responsive to a user request to perform processing of the verified database and creation of the sub-group database. In some embodiments of the invention, the server system includes a second processing utility configured to be responsive to a command from the first processing utility to generate a request to at least some of the identified individuals to provide additional data according to said one more parameters and conditions to thereby updating of the sub-group database. The second processing utility may be configured for updating the verified database with said additional data.

The first processing utility may be configured for using the sub-group database for collecting certain information from and/or delivering certain information to at least some of the identified individuals of the sub-group database.

The system may also be configured for constructing the verified database as described above. The server system(s) may be configured to present at least some of the identified individuals with a classified offer or provide certain targeted information.

In some embodiments of the invention, the sub-group database comprises a medical database comprising information pertaining to at least one of a disease, a medical condition, a genotype, a phenotype, a family relationship; and a geographic location of at least one of said identified individuals.

The processing of the verified database may include filtering the information in said database to create a sub-group of identified individuals. Then, at least one of a product and a service may be provided to at least one individual of said sub-group database. This may be responsive to the information pertaining to the at least one individual. The processing of the database may include geographical mapping of identified individuals of the sub-group. Providing of the individual (s) with at least one product or service may be responsive to the geographic location of the at least one individual.

In some embodiments of the invention, the processing of the verified database is aimed at constructing a family database for each individual. This may be carried out as follows: constructing at least two IDSs for corresponding at least two identified first individuals; identifying at least two IDSs having overlapping relationship data including at least one identical identified individual in the corresponding relationship data; and consolidating the at least two relationship data pieces to construct an expanded relationship data record. For example, an expanded family database may be constructed that comprises all family databases which are overlapping family databases and comprise data identifying the connection between individual of the expanded family database.

The results of the processing may be presented (displayed) to the individual(s). For example, an individual can receive information on his/her position in the relationship web or part thereof.

According to yet another broad aspect of the invention, there is provided a computerized system for managing and using a database over a computer network, the system comprising a server system linked to the network and accessible by users via their communication devices connectable to the network, said server system comprising a processor utility being associated with a verified database of a plurality of identified individuals comprising a plurality of individual-identifier data sets (IDSs) and relationship data and being adapted to process said verified database in accordance with one or more selected parameters or conditions and creating a sub-group database comprising data about at least some of the identified individuals characterized by said one or more selected parameters or conditions.

The processor utility may be configured to be responsive to a user request to perform the above processing of the verified database and creation of the sub-group database.

In some embodiments of the invention, the server system comprises a second processing utility configured to be responsive to a command from the first processing utility to generate a request to at least some of the identified individuals to provide additional data according to the one more parameters and conditions to thereby update the sub-group database and/or the main verified database.

The first processing utility may be configured for using the sub-group database for collecting certain information from and/delivering certain information to at least some of the identified individuals of said sub-group database.

According to yet further broad aspect of the invention, there is provided a computerized system for commercial use of a database of identified individuals operating over a computer network, comprising: one or more server systems linked to the network accessible by clients communicating over the network; the one or more server systems being configured to receive a plurality of individual-associated data bits (IDBs) entered by clients, the IDBs comprising personal identifiers and relationship data, the relationship data comprising data on one or more related individuals and the nature of relationship, to generate an individual-identifier data set (IDS), one for each identified individual, being either one of the users or one of the related individuals, to process all the IDSs to construct a verified database comprising IDSs of identified individuals and their position in a relationship web, and to process the information in said verified database according to at least one selected parameter or condition and create a corresponding sub-group database of at least some of said identified individuals.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 5 exemplifies an embodiment of comparing data bits on an individual obtained from two different IDBs;

DESCRIPTION OF THE INVENTION

Figure 1:
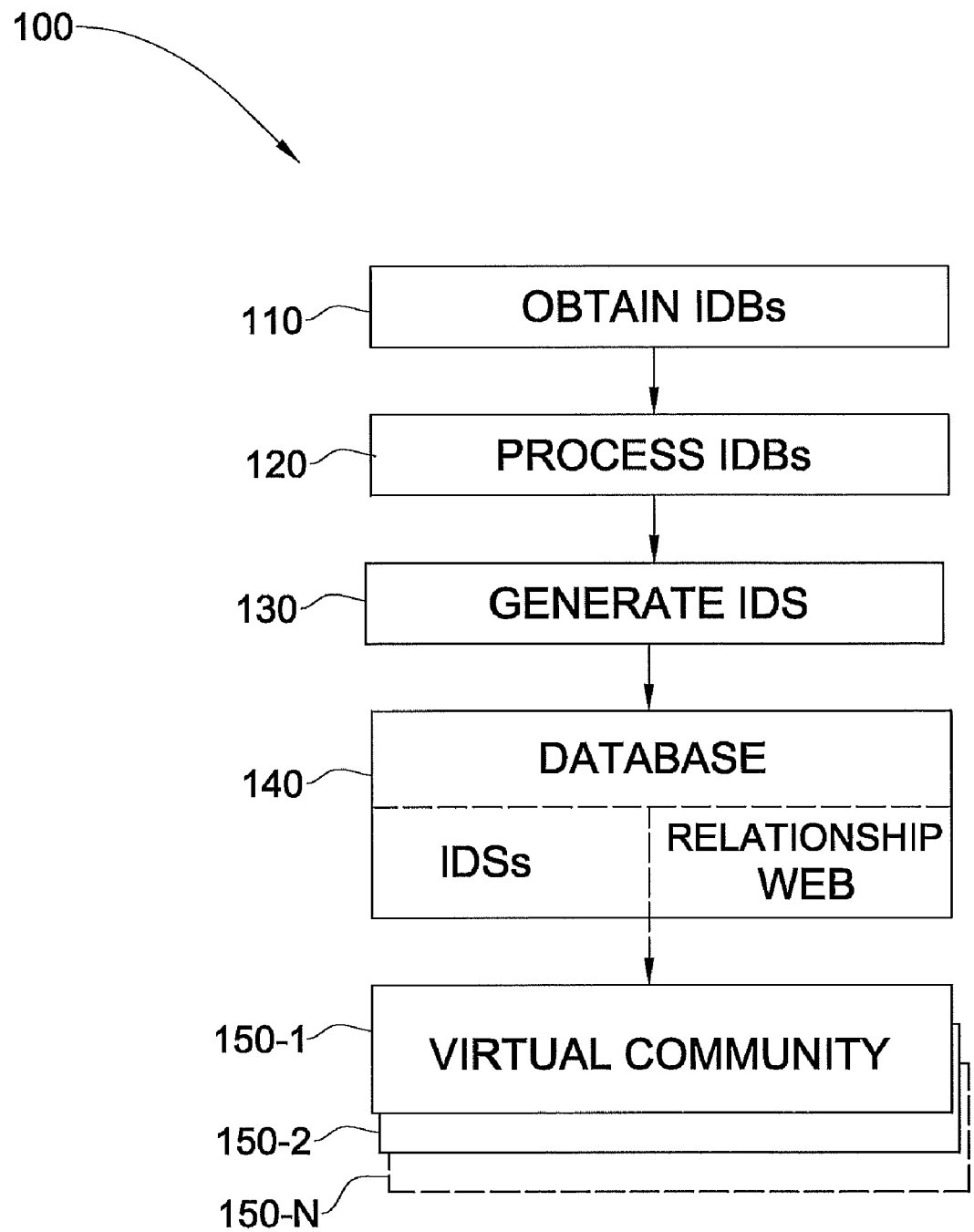
FIG. 1 is a simplified schematic flowchart illustrating an interactive method for constructing a main, users' related verified databases, useful for the purpose of the present invention.

In the present specification the words "individual" and "person" may be used interchangeably. The term "user" will be used to denote an individual who uses the system and the method described below and who enters or views data entered or database items generated in accordance with the invention.

The term "network" or "computer network", as used above and further below, denotes any communication network that permits many users to communicate with one another, exchange information and files, etc. The network is in particular the Internet, although not exclusively. The network may also be, for example, an Intranet. The term "network" should be construed in a broad sense as including different forms of communication that permit transmission of data between a plurality of data transceivers. This includes, but not limited to, computerized networks such as the Internet in which computerized devices, e.g. personal or handheld computers, can be employed for entering and/or receiving data; it may be a line telephone network, in which data may, for example, be entered through the use of the numerical keyboard, e.g. by following an audible menu; a cellular network, through which users communicate using mobile communication devices; and any combinations thereof.

For construction of the database useful for the applications subject of the invention, a plurality of users are permitted to enter individual-associated data bits (IDBs) into a computerized system. Each of the IDBs comprises at least one personal identifier relating to the user and relationship data comprising data on one or more related individuals and the nature of relationship. The IDBs are then processed to generate an individual-identifier data set (IDS), one for each identified individual, being either one of the users or one of the related individuals. A database comprising IDSs of identified individuals is thereby constructed.

The database comprises individual-identifying data records constructed by processing a plurality of individual-associated data bits (IDBs) entered by a plurality of users of a computerized system. Each IDB comprises at least one personal identifier on the user and relationship data on one or more related individuals and the nature of relationship. An individual-identifier data set (IDS) is thus constructed, one for each identified individual, which either one of said users or one of said related individuals. A database comprising IDSs for identified individuals and their position in a relationship web is eventually generated.

The term "permitting" used above and further below denotes providing individuals with an access to perform the action specified. This may be, by one embodiment, broadcasting a user interface consisting of one or more electronic forms or pages over a computer network, in which individuals can enter data. The user interface has typically data entry fields for entry of the IDBs. The fields may include fixed fields where data may be entered in the form of text, by selecting or marking one of plurality of options, by free text entry fields, etc. Such filed may include essential fields and optional fields. By another embodiment, this may include providing users with the ability to transmit an electronic file containing the data. Such an electronic file may be transmitted over the network, or may be transmitted off-line through any other suitable carrier of electronic information such as CD-ROM, a magnetic disk, a flash card, etc. As is clear, the invention is not limited by the manner in which the data is entered.

The term "individual-associated data bits" or "IDBs" denotes a group of data pieces that relate to the individual entering the data. Each of the IDBs may be unique for a specific individual and may include a minimum set of data that permits to identify an individual at a certain degree of probability and includes some personal identifiers and relationship data. The IDBs comprise both personal identifiers and relationship data, defined below. The IDBs may also include other data pieces such as family stories, information entered by a data-entering individual for the benefit of others that view his IDB and in general any information a data-entering individual wishes to associate with data related to him/her.

The term "personal identifiers" denotes pieces of data on an individual. The personal identifier of an individual may be entered by that individual or may, at times, be entered by other users to form the IDS (defined below). Personal identifiers may include formal identifiers such as name, address, birth date, etc., and other identifiers such education, profession, interests, hobbies, health data, blood type, tissue type, genetic profile, martial status, etc. The entered data may typically include a minimum set of data that can jointly identify an individual with some degree of probability. Said minimum set of data typically include a combination of identifiers that distinguish the specific individual from others; namely the chance of mistaking such an individual for another is relatively low. Said minimum set of data should preferably be entered both with respect to the personal identifiers as well as with respect to the relationship data. Such minimum set of data typically include familial data, namely at least some data relating to the individuals family.

The term "relationship data" denotes pieces of data that relate to individuals that the data-entering individual has some form of relationship with. Particular example includes other individuals with whom the data-entering individual has some form of family ties. These may include first degree family members (parents, brothers and sisters, spouse, children) as well as further (second, third, etc.) degree family members (grandparents, cousins, in-laws, etc.). The family members included in the relationship data may be living and/or dead. In addition, the relationship data may also include data on other type of related individuals including friends, acquaintances, neighbors, business colleagues or associates, members of societies or organizations to which the individual belongs, and others. The relationship data, in addition to including some formal identifiers of the related individuals, includes also data relating to the type of relationship, whether it is past and/or present relationship, etc.

The term "individual-identifier data set" or "IDS" denotes a set of data pertaining to an identified individual. The IDBs entered by an individual are processed to generate an IDS for each identified individual. The IDS may include data based on that entered by the entering individual, optionally differently arranged; or may be refined data, namely data that was initially processed, for example: to correct inherent inconsistencies; eliminate data which is inherently inconsistent and the inconsistency cannot be resolved; data corrected on the basis of IDBs entered by other individuals (see below); ascribing a reliability score to each of the IDBs (see below); etc. In its basic form, the IDS is based on the IDBs entered by an individual user. In fact an IDS will be constructed for every identified individual for whom personal identifiers were included in entered IDBs. This includes an IDS for the data-entering individual and any other identified individual for whom personal identifiers were included among the IDBs. Initially, the IDS may be constructed on the basis of IDBs entered by a single individual user. Once more IDBs are entered by different users, data on identified individuals may also be entered an included in IDBs of other users and once processed it may be included in an IDS for that identified individual, which may be either a new IDS if that identified individual was not hitherto included in the system or may be additional data added to an already existing IDS of an identified individual. The IDS for an identified individual may thus be continuously updated upon relevant data entry by other individuals.

It is possible that the IDBs do not contain sufficient information for unequivocal one-to-one identification of each identified individual. For example, an IDB of person A may include relationship data on person B with personal identifiers that include the name of person B and the nature of relationships between person A and person B. This information may be insufficient to unequivocally identify person B. Similarly, some personal identifiers of person B may also be included in IDBs entered by another person C. Thus, initially, two separate IDSs may be formed for person B. Once the two IDSs are being recognized as belonging to the same person A, the data included in them may be consolidated into one IDS.

The IDSs are typically constructed from IDBs entered by two or more different individuals. Thus, in accordance with an embodiment of the invention, at least one IDS, but preferably a plurality of IDSs are each constructed from IDBs entered by two or more individuals. As will also be noted further below, IDSs may be updated by newly entered relevant IDBs (namely IDBs including data relating to the identified individual associated with the IDS to be updated), typically on an on-going basis.

The term "individual" in a phrase such as "individual associated with the IDS" or "IDS associated with an individual" or any other phrase with a similar meaning, is being used herein to denote the individual who is the subject of the IDS (the primary record in the IDS relates to that individual).

The term "identified individual" relates to each individual, datum on whom was included in one or more entered IDBs. This includes the data-entering individual and any related individual included in the user's entered IDBs.

The term "relationship web" refers to a virtual web of nodes and lines, each node being one of the identified individuals and the lines, being relationship lines (see below) connect each node to one or more other nodes in the relationship web. Each such line may also have associated identifiers that define the type of relationship between the two individuals. The term "relationship web" should not be construed only in a graphical sense. Rather, the relationship web may be represented in many different representations including that of nodes and lines or any other graphical representation manner, in a form of data tables, it may be a virtual web generated within a computer, etc.

The term "relationship line" will be used to define a direct relationship link between individuals in the relationship web (a direct relationship link being, for example, first degree family, personal friends, business colleagues, etc. Distance between individuals in a relationship web may thus be defined in terms of a number of relationship lines. For example, three relationship lines to an individual in a relationship web of friends, mean a friend of a friend of a friend. As another example, two or three connecting lines to an individual in a family tree mean, respectively, a second degree (e.g. grandparent, grandson, uncle, brother/sister-in-law, etc.) or a third degree (first cousin, great grandparent, etc.) family ties.

The commercial use of the database may be through a computerized system operating over a computer network. Such system comprises one or more system servers linked to the network accessible by clients communicating over the network; said one or more servers being configured to receive a plurality of individual-associated data bits (IDBs) entered by clients.

The commercial application, which may be online or offline provided, may, for example, include: applications in human medicine, e.g. for tracing and treating familial diseases; sectorial and targeted marketing; demographic population studies; identifying a hostile person, a lost person, a relationship between a deceased person and living person; formation of a family portal; and many others.

The computerized system is preferably operative over a computer network such as the Internet and typically comprises one or more appropriately configured servers, linked to the network. Individuals can then access the system through the network.

The relationship web may, typically, be constructed and presented in the form of family tree in which each identified individual is presented as a node and the relationship web as connectors between nodes.

The term "family tree" used in this patent specification should be construed in a broad sense as relating to a data base of a few persons and at least some of their familial relationship. The family tree may be represented graphically in one of many different graphical representation means of such information; may be stored as data records within a computer (the data record including at least one identifier for each person and one or more family relationships to one or more other individuals in the family tree); or both. A family tree may also be thought of as a graph (which may be graphically represented or be a virtual representation within a computer) in which connecting lines represent the family relationships and the nodes represent the persons of the family tree (to be referred to herein at times as "nodes"). The term "family tree" should thus be expansively construed to include any model for organizing one or more data repositories in a hierarchical arrangement comprising at least parent and children nodes. It should be understood that a tree may be of different complexity, e.g. be as simple as one parent and one child, as complex as the theoretical "single family tree" that links all data in the repositories, etc.; two or more trees may overlap, or one tree may completely include one or more other trees.

The relationship web may include family trees that are merged together to yield merged and enlarged family trees.

The entered IDBs, that will subsequently be included in the IDS associated with the data-entering individual, may also include personal data that, once included in the database, may benefit an individual (the data-entering individual, or another) under defined circumstances. Such data may, for example, be blood type, histocompatability data, genetic data, etc. In case of a surgery, blood transfusion or another emergency medical procedure, this will permit a rapid search for a suitable donor of blood, tissue, etc. By another example, by entering various personal descriptors such as personal interests, hobbies or occupation, personal history or background, etc., typically inserted in dedicated fields, sub-group databases may be constructed based thereon. For example, a sub-group database for individuals that have all a common medical history or physiological parameter, e.g. blood or tissue type, or physiological condition (certain disease) may be constructed.

Typically with more data on an individual, preferably classified, there may be an increase in the number and/or extent of uses in accordance with the invention. For example, certain data on individuals may permit to associate individuals with other individuals with matching personal descriptors which may then made part of a virtual community (see below). Such association may be defined through inclusion in a sub-group database. Becoming a member of a virtual community may be beneficial as it may serve as a forum for exchange of ideas, for coordinating activities, for business transactions, etc. Data entered into an IDB may include information which may be broadcasted over the computer network or shared with others. Also, personal descriptors may permit to provide, in accordance with the invention, targeted services, information, offers, etc.

The IDS is a personal data record that typically comprises a main data record including data on a first person, which is the individual associated with the personal data record, and one or more sub-records including personal identifiers on one or more second, related persons and the nature of their relations (including, but not limited, to family ties) to the first person. The sub-records may include data other than the personal identifiers and the relationship data may at times include links to such data included, for example, in the IDSs of the second persons. The IDS may be a product of consolidation of data from a plurality of IDBs that include data on the first person or data on relationship of second persons to the first person. For example, a person A who is a cousin of person B and a sibling of person C may have its name and possibly other identifiers included in IDBs entered by persons B and C. Thus, an IDS can be constructed for person A, in which any personal attributes about him, including his name, comprised in the IDBs entered by persons B and C will be included in the main record of such IDS, which will include also sub-records assigned to persons B and C identifying them as a cousin and sibling, respectively.

The processing of the IDB-originating data may comprise a verification procedure of one or more of the IDBs entered by an individual through comparison with IDBs entered by one or more other individuals. A data bit included among the IDBs entered by an individual that is verified through data bits included in the IDBs of one or more other individuals, has an a priori higher probability of being correct than a non-verified data bit. Furthermore, verification of a number of data bits included in the IDBs of one individual through data entered by another, may provide a measure of reliability of the entered data and thus serve as an indirect measure of verification of data bits that were not verified by the IDBs of one or more other individuals.

The verification process may include ascribing a reliability score to data bits included in the IDBs of an individual to the entire IDBs, to the IDS produced on the basis thereof or a portion thereof, e.g. a reliability score to the personal identifier of the individual associated with the IDS, based on the extent of data verification. The reliability score may be based on the degree of correspondence between the IDBs entered by different individuals. By one embodiment, a reliability score is ascribed to each of the data pieces entered by an individual. Additionally, an overall reliability score for the IDS or at least the personal identifiers of the associated individual may be calculated, e.g. based on the reliability scores of the different IDBs. Other factors that may influence the reliability score include the extent of relationship data on related individuals included in the IDS, namely the number of relationship lines linking the identified individual to other identified individuals, and the reliability score of the related individuals identified in the IDS.

The reliability score or a reliability indicator based thereon may be included in the database. The reliability indicator may, for example be graded between poor to good, may be a score, e.g. from 1 to 10, etc. The reliability score may be made to be accessible to users who review the IDS of an identified individual to permit them to get a sense on the IDS's reliability. At times the IDS of an identified individual will be included in the database only if it is equal or greater than a predetermined value. The IDSs then form the basis for a database of identified individuals. An important feature of the database is that it includes also the position of the individual in a relationship web, said position being definable through the links of any individual to others.

The relationship web, or typically only portions thereof relevant for an identified individual, may be represented to the individual in one or more of a variety of different ways. It may be represented in the form of nodes and connecting lines, as described above. By way of an illustrative example, each node may appear with some basic identifiers, e.g. name, address or picture, and then each node may hyperlink to a more detailed description or a web page of the specific individual. By way of another example, the relationship web may be represented in one of a variety of graphical representation means for representing family trees. The viewing user may be permitted to 'navigate' through the relationship web, for example through moving a cursor to different nodes and possibly viewing node-related data, i.e. the IDS or part thereof, e.g. by 'clicking' on a node. As will be appreciated such a navigation mode is a non-limiting illustrative example only.

The relationship web may be presented such that a node representing the viewing user is in the center with lines connecting his associated node to all his related individuals. In the case of a family relation, for example, direct lines may typically connect to first degree relations and indirect lines, namely lines that lead through a point representing another individual may connect to second and further degree relatives, e.g. a line to a grandparent or a nephew, will connect through a parent and a sibling, respectively. This manner of display as described above is not limiting but rather an illustrative example. By way of another example, while navigating through the relationship web, the individual which is the focus of review may be displayed in the center. Furthermore, graphic display of the relationship web is also only a non-limiting illustrative embodiment. For example, the relationship web for an individual may be presented in the form of a table listing the various relations under different categories, possibly with hyperlinks to the mentioned individuals.

The relationship web for an identified individual may include a variety of different types of relationships. One type of relationships are such entered as part of the IDBs and may include family; current friends, business associates, co-members of organizations or societies, employees, employers, work colleagues, etc.; past friends, business associates, co-members of organizations or societies, employees, employers, work colleagues, etc. However, there may also be other types of relationships that may be entered by the computerized system. For example, where an identified individual is identified as one with a certain scope of interest, hobby, as one having a specific background or origin, etc., the relationship web may be constructed to include other individuals with similar scope of interest, hobby, background or origin, etc., either globally, one linked to a certain geographic location and so forth.

The family of an individual, including identifiers of family members and the nature of the relationship of other family members with the individual, typically provides a clear and unequivocal identification of a specific individual. For constructing a database a plurality of individual-associated data bits (IDBs) entered by a plurality of users of a computerized system are processed. Each of the IDBS comprises personal identifiers and relationship data comprising data on one or more family-related individuals and the nature of relationship. In this manner an individual-identifier data set (IDS) is obtained, one for each identified individual, being either one of said users or one of said related individuals. All the IDSs are processed to construct a database comprising IDSs of identified individuals. The database may also provide an indication of the position of the identified individuals in a relationship web.

Different identified individuals in a family web have different family relationships. In other words, the family relationships of different individuals, even within the same family, will have only a partial overlap with one another. By virtue of such a partial overlap, once a family of one individual becomes linked to another and then to that of another and so forth, this may yield, eventually, an essentially global relationship web.

The IDS for each first individual includes data on other, second individuals with whom the first individual has some form of relationship, particularly, but not exclusively, family relationships. Thus, the IDS of each individual may be viewed as a relationship databases, in particular a family database of individuals related to said first individual. Thus, two or more IDSs that have at least one overlapping node may provide a basis for merging of relationship webs, particularly family trees, to one another. Thus, at least two constructed IDSs for corresponding at least two identified first individuals are constructed; at least two IDSs having overlapping relationship data records including at least one identical identified individual in the corresponding relationship data records are identified; and then the at least two relationship data records are consolidated to construct an expanded relationship data record. A specific example involves the construction of an expanded family data record.

The relationship web may also have different layers. For example one layer of family, another layer of friends, a further layer of business colleagues, etc.

The relationship web may also be displayed in a hierarchical way. For example, in the case of an individual with a common interest or hobby, as there may be large number of individuals with such an interest or hobby, rather then showing a link to each individual with the same interest or hobby, the relationship web may provide a link to a webpage, for example, that will link all individual in a given region or location sharing the same interest or hobby. Such a webpage may then link to individual sharing the same interest or hobby in other regions or locations; or a link to a global webpage of individuals with the shared interest or hobby, which will have links to regional web pages of such individuals and so forth, eventually down to the level of the different individuals.

While it is possible to permit an identified individual to review the entire relationship web, in a typical mode of implementation of the invention, the individual is permitted to review only a portion thereof relevant to that individual (such portion to be referred to, in some places, as "individual relationship web"). Such portion may be a system-wide predefined portion. For example, an individual relationship web of family members may include all family relationships up to a certain distance, namely up to a certain relationship lines distance. As another example, a relationship web of friends or business colleagues may also have a limit, e.g. up to two lines, i.e. a friend of a friend or a business colleague of a business colleague, respectively.

By another example, in addition or in the alternative, each identified individual may be given the option of defining the level of his/her 'visibility' to other individuals, namely defining the portions of the IDS that my be reviewed by users. For example, an individual may be given the option of defining permissions to viewing the IDS or portion thereof, e.g. based on distance in terms of number of relationship lines or by another relationship parameter, based on a certain profile (such as all individuals with a certain defined scope of interest, residence in a certain geographical location, etc.), or using any other criterion.

Any identified individual may also, according to an embodiment of the invention, define the extent in which his IDS or portions thereof should be privileged. Also, under another embodiment, each identified individual may define or provide criteria on identified individual that may not be entitled to review all or portions of his IDS. The permissions and/or privilege criteria may apply to the entire IDS or portions thereof. Also, different criteria may be applied to different portions of an IDS.

As will be appreciated, the relationship web is not static but is rather dynamic and grows upon addition of identified individuals, additional relationship lines and additions or updates to the already existing IDSs, as more users of the network enter their IDBs. On some occasions a new user who newly enters his IDBs may already be an identified individual through the IDBs entered by another individual. On other occasions such a new user may not be an identified individual but one or more of his related individuals may already be an identified individual. On other occasions both a new user and his related individuals may be new to the system. In the two former cases, the newly entered data will be incorporated in the already existing relationship web. In the latter case, the entered data will form an independent separate relationship web until such time as it will become linked through new data entered by later new users.

An identified individual may receive an automatic notification, e.g. to a computerized or other communication device associated with the individual or to an electronic address associated with him in case of developments relating to him or his relationship web, i.e. updates in his IDS through IDBs added by others; for example, new data relating to him, new family members added to his family tree, new or updated data on existing individuals in his relationship web entered by other users, and a variety of other news relating to his relationship web. The computerized device may, for example be a computer in which case the notification may be an email; a communication device may, for example, be a mobile communication device and the notification may be in the form of an SMS message.

Another use of the method and system of the invention is in commercial applications based on identified relationships between individuals. The main database, constructed as described above, and including all the IDSs and the relationship data is used for at least one commercial application. For example, a sub-group database may be created from the contents of the main database and possibly from additionally requested information, according to one or more predetermined criteria to enable classified proposals or information to selected users.

The method according to an embodiment of the invention comprises: providing a server system that is capable of filtering or mapping the contents of the main database to permit to channel classified information or proposals to selected users. The server thus selects users to receive specific proposals or information.

In accordance with an embodiment of the invention, an association, group or a constructed virtual community of individuals may provide a useful means for promoting sales of a product or service within the common scope of interest of individuals of such association, group or virtual community. Such sales promotion may be through distribution of electronic promotion material, placing advertisements on relevant virtual bulletin boards, etc. The target individuals, according to some embodiments, may be a group of individuals sharing all one or more common identifiers.

The database generated in accordance with the invention is another of its aspects. Such a database may be a highly useful tool for demographic research. Such use constitutes an additional aspect of the invention. Thus, the database of the invention may be useful for data mining. In addition, the database may be useful for conducting of surveys or opinion polls, etc. In the latter case, the database may be used for sending questionnaires to individuals with specific, predefined profiles.

The database of the present invention may be used for commercial purposes, exemplified, but not limited to, the examples described hereinbelow.

Some embodiments of the present invention are directed to using the database for marketing. In some cases, the marketing application is a sectorial marketing application selected from an on-line and an offline sectorial marketing application.

Some further embodiments of the present invention are directed to using the database for advertising. In some cases, the advertising is selected from electronic media advertising, paper media advertising and banner advertising.

Some additional embodiments of the present invention are directed to using the database for a statistical or demographic research application. The statistical application may be selected from gathering statistics relating to at least one of a family, a geographic sector, a political sector and a virtual community.

This invention is further directed to methods for using the database for a medical application. The medical application may be selected from one pertaining to a blood-related disease, e.g. finding a donor for a blood transfusion or a blood component transplant, one pertaining to a genetic disease, a personalized medical treatment and others.

DETAILED DESCRIPTION OF SPECIFIC EMBODIMENTS

In the detailed description, numerous specific details are set forth in order to provide an understanding of the invention. However, it will be understood by those skilled in the art that these are specific embodiments and that the present invention may be practiced also in different ways that embody the characterizing features of the invention as described and claimed herein.

Unless specifically stated otherwise, as apparent from the following discussions, it is appreciated that throughout the specification discussions utilizing terms such as "processing", "computing", "calculating", "determining", "deriving", "generating" or the like, refer to the action and/or processes of a computer or computing system, or processor or similar electronic computing device, that manipulate and/or transform data represented as physical, such as electronic, quantities within the computing system's registers and/or memories into other data, similarly represented as physical quantities within the computing system's memories, registers or other such information storage, transmission or display devices.

Embodiments of the present invention may use terms such as, processor, computer, apparatus, system, sub-system, module, unit, device (in single or plural form) for performing the operations herein. This may be specially constructed for the desired purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, Disk-on-Key, smart cards (e.g. SIM, chip cards, etc.), magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions capable of being conveyed via a computer system bus.

The processors/devices presented herein are not inherently related to any particular electronic component or other apparatus, unless specifically stated otherwise. Various general purpose components may be used in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Similarly, the computerized system described herein is also not necessarily related to a specific physical entity. The computerized system may use general components, such as servers, routers, etc., or may use specialized apparatuses design specifically for use in accordance with the teaching of the invention.

It should be understood that the methods of the present invention are exemplified by the figures herein, but not limited thereto.

Reference is now made to FIG. 1, which is a simplified schematic flowchart 100 illustrating a manner of constructing a main, users' related database, useful for the purposes of the present invention.

Users are permitted to enter individual-associated data bits (IDBs) into a computerized system (step 110). The obtained IDBs include each a personal identifier, which includes data relating to the user and relationship data. The relationship data includes data on the user himself and data on one or more related individuals, typically, although not exclusively, individuals related to the data-entering individual by family. The relationship data also includes data on the nature of relationship with the related individuals (e.g. child, parent, sibling, etc.). The IDBs are processed (step 120), to generate IDSs (step 130), one for each identified individual. A verified database of IDSs is then constructed (step 140) which includes the IDSs of all identified individuals 142 and a relationship web 144, the latter including data on the relationship links between identified individuals. The relationship web may be one merged relationship web from all individuals or may include a plurality of such webs for different groups of identified individuals.

Figure 2:
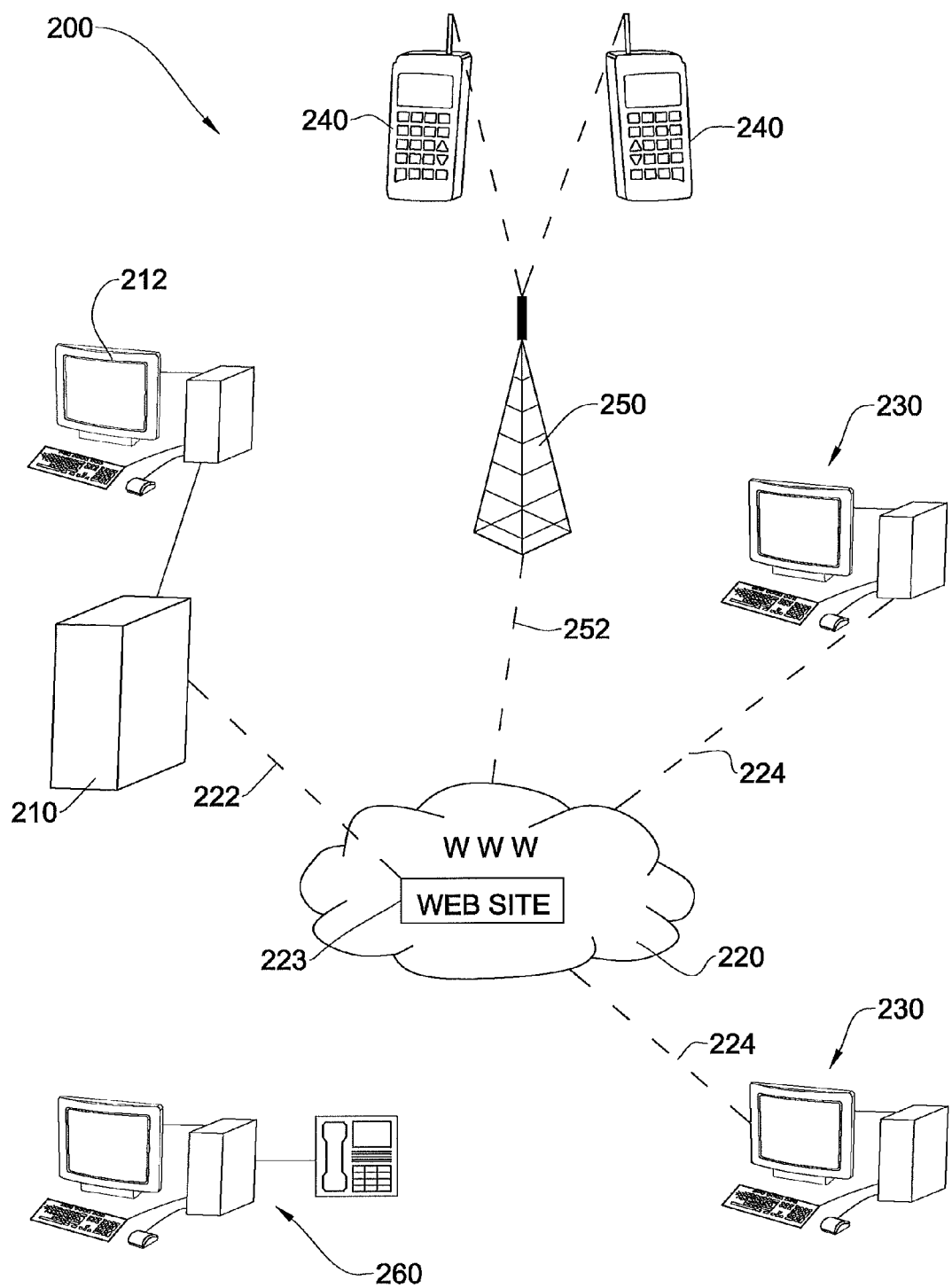
FIG. 2 a schematic pictorial illustration of a computer system 200 for creating a database of users' related data in accordance with an embodiment of the present invention

Reference is now made to FIG. 2, which is a schematic pictorial illustration of a computer system 200 for creating a database of users' related data in accordance with an embodiment of the present invention.

It should be understood that many variations to this system are envisaged, and this embodiment should not be construed as limiting. For example, a facsimile system or a phone device (wired telephone or mobile phone) may be designed to be connectable to a computer network (e.g. the Internet). Interactive televisions may be used for inputting and receiving data from the Internet. In some cases, the systems described herein may communicate via Intranet, Internet and combinations thereof. Additionally, new methods and systems for communication, beyond those of the existing Intranet/Internet are deemed to be usable for the methods of the present invention.

System 200 typically includes a server utility 210, which may include one or a plurality of servers and one or more control computer terminals 212 for programming, troubleshooting servicing and other functions. Server utility 210 is linked to the Internet 220 (constituting a computer network) through link 222, for running system website 223 and for communication with the users. Users may communicate with the server through a plurality of user computers 230, which may be mainframe computers with terminals that permit individual to access a network, personal computers, portable computers, small hand-held computers and other, that are linked to the Internet 220 through a plurality of links 224. The Internet link of each of computers 230 may be direct through a landline or a wireless line, or may be indirect, for example through an intranet that is linked through an appropriate server to the Internet. The system may also operate through communication protocols between computers over the Internet which technique is known to a person versed in the art and will not be elaborated herein. Users may also communicate with the system through portable communication devices such as $3^{rd}$ generation mobile phones 240, communicating with the Internet through a corresponding communication system (e.g. cellular system) 250 connectable to the Internet through link 252. As will readily be appreciated, this is a very simplified description, although the details should be clear to the artisan. Also, it should be noted that the invention is not limited to the user-associated communication devices—computers and portable and mobile communication devices—and a variety of others such as an interactive television system may also be used. The system 200 also typically includes at least one call and/or user support center 260. The service center typically provides both on-line and off-line services to users from the at least one professional. The server system 210 is configured according to the invention to carry out the above-described method for creating the main verified database including the IDSs of all identified individuals and the relationship web, based on data received from the users, being initiated in either pull or push mode.

Figure 3A:
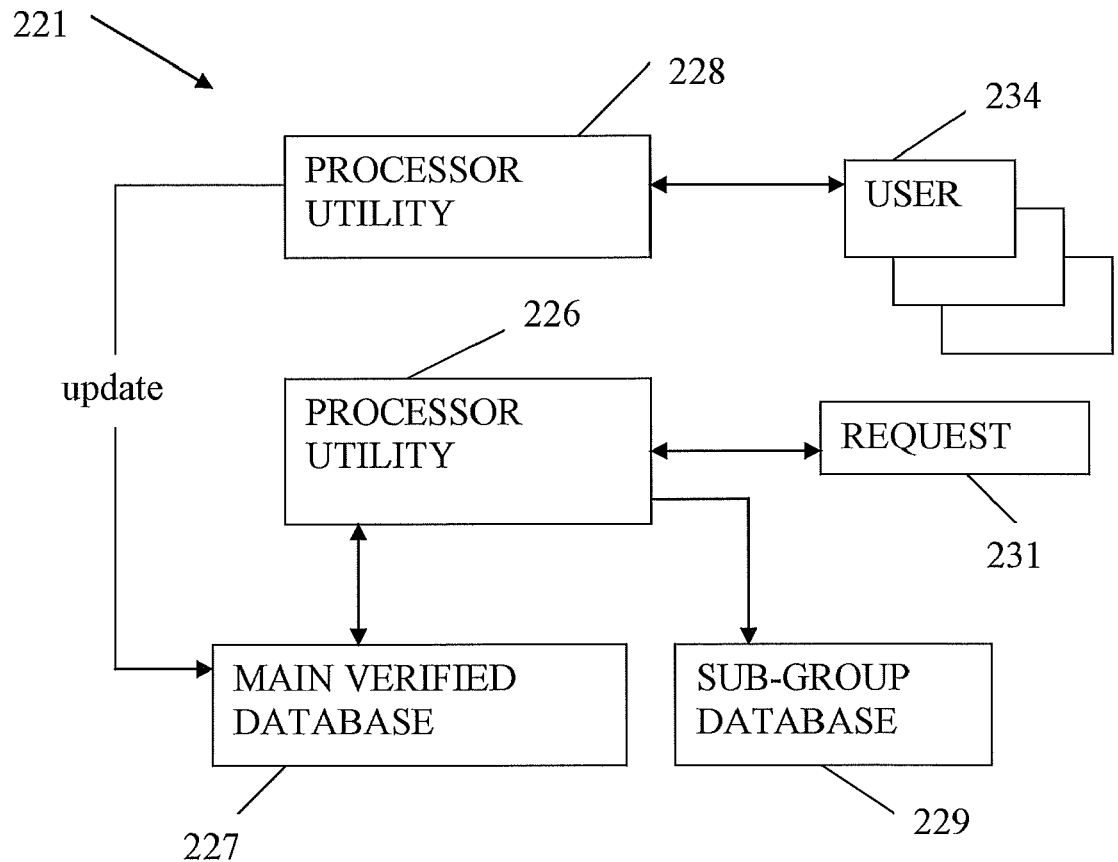
FIG. 3A illustrates a block diagram of a database managing system according to an embodiment of the invention.

Reference is now made to FIG. 3A, which is a block diagram of a database managing system 221 according to an embodiment of the invention. System 221 is configured as a server system, in the meaning that it is a computer system linked to a communication network (e.g. the Internet) and is accessible by users from their personal communication devices (computer, mobile phones) via the Internet. System 221 is configured for using individuals' related data contained in the main verified database 227 constructed as described above (i.e., database of IDSs of all identified individuals and a relationship web) according to one or more selected parameters. System 221 may be a constructional part (software/hardware utility) of the server utility (210 in FIG. 2) that creates the main verified database, or may be a separate server system connectable to the main database e.g. via the server utility 210. Also, system 221 is associated with its website which is accessible to users and which may or may not be a part of website 223 of FIG. 2.

Database managing system 221 comprises inter alia a data processing utility 226 for processing contents of the main, verified database 227 of identified individuals. The system is configured for creating one or more sub-group databases 229 in accordance with one or more predetermined parameters and/or according to a request 231 inputted to the system and fed to the processor utility 226. Such a request or predetermined parameter may, for example, be: a medical parameter, e.g. all individuals having a specific tissue type; a location parameter, e.g. all individuals living in a specific geographical location; etc. Another processor utility 228 is configured for communication with users 234. For example, in case some of the users' related data records in the main verified database 227 lack certain data relevant to the predetermined parameter or request, processor utility 226 operates the processor utility 228 to initiate communication with the respective users to request such data. After user input, such data may be added to main database 227 and if relevant may be used to create or update the respective sub-group database 229. Processor utility 226 may also operate the processor utility 228 to distribute certain data from a sub-group database 229 to users or a selected group thereof or distribute certain data to users included in database 229.

For example, a sub-group database 229 may be formed to include data on all individuals suffering from a certain diseases. Data relating to therapy of such a disease may be distributed to such users. Medical data relating to users from the sub-group 229 may be transferred to a medical center, where these data are further analyzed for research or service providing purposes.

Another example is a subgroup database formed for individuals residing in a certain location and such individuals may then receive offers or promotional material relating to a product or service provided in their vicinity. Additionally, a user may request to locate service providers in a specific location and the system may then create a respective sub-group database and forward information on the content to the requester, at times after obtaining necessary permission from such service providers.

Figure 3B:
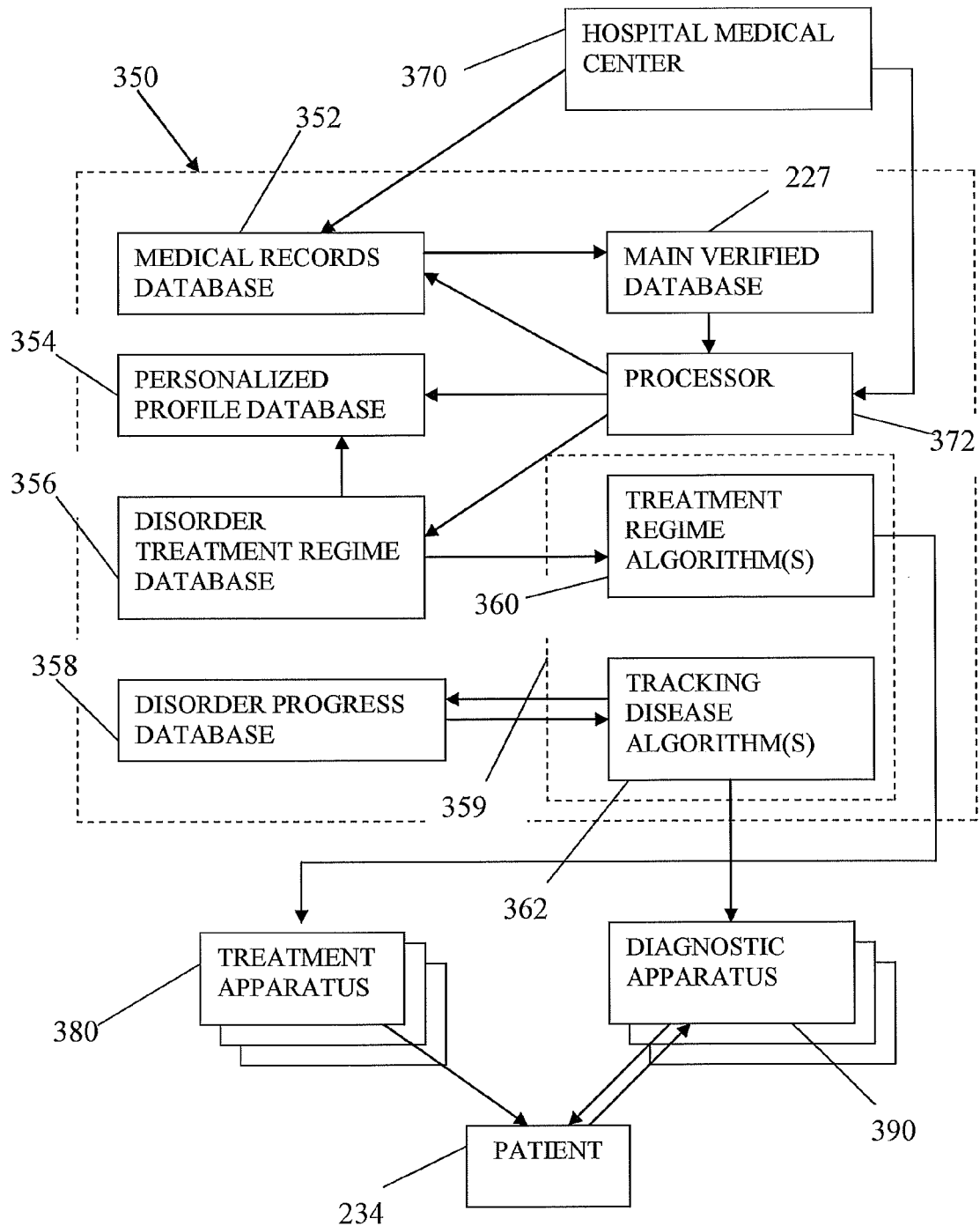
FIG. 3B is a simplified block diagram of an interactive system 350 for providing users/patients with a personalized medicine service.

Reference is now made to FIG. 3B, which is a simplified block diagram of an interactive system 350 for providing personalized medicine, which may be used in addition to or instead of the system of FIG. 3A, in accordance with an embodiment of the present invention.

This figure shows the link of the interactive system 350 via a hospital/medical center 370 to provide diagnosis and/or treatment to an individual. System 350 is configured a server system which may be a constructional part of the server system 210 of FIG. 2 for constructing the main verified database 227 or may be a separate server system connectable to the server 210. The system 350 is associated with a memory utility for storing the following databases: a medical records database 352, a personalized profile database 354, a disorder treatment database 356; and a disorder progress monitoring database 358. The system 350 includes a processor utility 359 having a module 360 for running a treatment regime algorithm and module(s) 362 for running one or more tracking disease algorithms 362. It should be understood that the memory utility may be entirely a part of the system 350 or may be distributed between several computerized systems communicatable with one another via a communication network. In other words, some of the databases or parts thereof may be external to system 350, but may be in communication therewith. For example, medical records database 352 may be retained outside system 350, e.g. may exist at the hospital/medical center 370 and provided/copied to system 350.

The system 350 receives information from one or more hospitals/medical centers 370. The hospitals/medical centers may provide updated personalized medical records of one or many patients. The personalized medical records in database 352 may be collated with personalized profiles from the personalized profile database 354 in a number of different ways. The system 350 includes a processor utility 372 configured and operable to continuously update the personalized profiles database 354 based on data in the main verified database 227.

It should be understood that medical centers wishing to use a personalized medicine methodology may wish to have additions made to their medical records, based on the authenticated data in the main verified database 227. The medical center may pay a fee for each piece of data received from the system 350 or may alternatively, pay a subscription fee to the service providers of database 227. Additionally or alternatively, the personalized profile database 354 may be updated with authenticated information from database 352. However, this data of database 352 is be verified and authenticated by methods such as those illustrated by FIGS. 4-6B hereinbelow, before being transferred to database 354.

According to some embodiments, there may be several stand-alone systems 350 that do not interact directly with each other, but are configured and constructed to allow the import/export of verified data from one system to another such system, using the methods for data verification/authentication described herein.

One or more treatment apparatus modules 380 may be activated to treat a patient/user 234 via the system 350 from at least one hospital/medical center 370 and/or by treatment regime algorithm 360 of the system 350.

Additionally or alternatively, one or more diagnostic apparatus modules 390 may be activated to diagnose a patient/user 234 via the system 350 from at least one hospital/medical center 370 and/or from tracking disease algorithm 362 of system 350.

The methods of using system 350 of the present invention are exemplified by FIGS. 11-13 hereinbelow, but are not limited thereto.

It should further be understood that system 350 can be used for updating personalized medical records in database 352 in real-time from hospital/medical center 370. The personalized medical records in database 352 can also be in real-time updated with data from the verified database 227 and/or or from database 354, which in turn can be real-time updated with data from the verified database 227 as well as from database 352. Data from medical records database 352 as well as from personalized profiles database 354 can also be used for updating the disorder treatment regime database 356 and/or the disorder progress database 358, in real-time. Data in any one or more of databases 352, 354, 356 and 358 can be used to perform at least one of treatment algorithm 360 and tracking disease algorithm 362. User/patient 234 can be treated with treatment apparatus 380 according to at least one of his medical record in database 352, his personalized profile in database 354, his updated disorder treatment regime in database 356, his disorder progress in database 358. Also, a patient can be treated based on measurements taken by diagnostic apparatus 390 and transferred to hospital/medical center 370 and/or based on tracking disease algorithm 362. The results of treatment regime algorithm 360 can be used for updating at least one of databases 352, 354, 356 and 358 per treatment step hereinabove. User/patient 234 can be diagnosed with diagnostic apparatus 390 and data from apparatus 390 can be transferred to at least one of hospital/medical center 370 and can be used for operating the tracking disease algorithm 362. Also, the results of tracking disease algorithm 362 can be used for updating at least one of databases 352, 354, 356 and 358 responsive to diagnosis step hereinabove.

Figure 4:
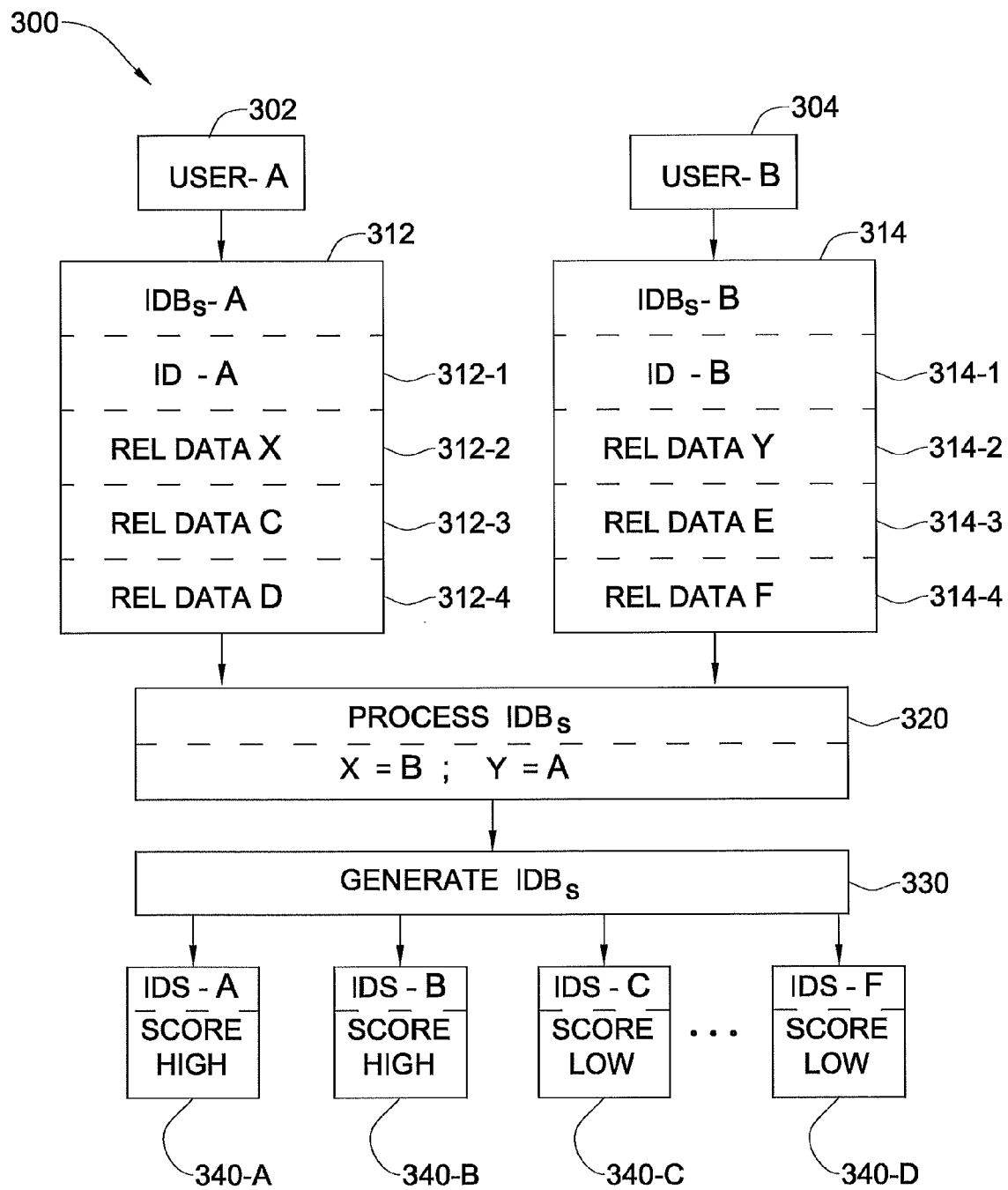
FIG. 4 is a simplified schematic flowchart illustrating a method for constructing IDSs and ascribing a reliability score in accordance with an embodiment of the present invention.

Reference is now made to FIG. 4, which is a simplified scheme of IDBs received from two users—User-A 302 and User-B 304—and processed, for example as described above with reference to FIG. 1.

User-A and User-B input respective IDBs, IDBs-A 312 and IDBs-B 314. IDBs-A 312 includes personal identifiers of User-A 312-1 and relationship data pieces 312-2, 312-3 and 312-4 on related individuals X, C and D, respectively. The IDBs-B 314 similarly includes corresponding data pieces 314-1 through 314-4 on related individuals B, Y, E and F. As will be appreciated the personal identifiers 312-1 and 314-1 consist of a plurality of data bits that may characterize each of users A and B. Similarly, relationship data 312-2, 314-2 through 312-4, 314-4 include personal identifiers of the individuals as well as relationship data identifying the nature of the relationship between each of the users A and B to the related individuals.

As will also be appreciated, the example presented herein in which there are 3 related individuals in each of the IDBs is but an example and any number of related individuals may be included in the IDBs.

Upon processing of the IDBs (step 320) the computer system identifies that related individual X and Y are individuals B and A, respectively. In the next step 330 IDSs are generated. In total, the two IDBs 312 and 314 relate to 6 identified individuals and accordingly from these two IDBs a total of 6 IDSs 340-A, 340-B, 340-F can be generated for individuals A, B, . . . , F, respectively. A reliability score for each of these IDSs may also be generated. As IDS-A 340-A and IDS-B 340-B are generated each from data included in two IDBs, the relative reliability score that may be generated may be high as compared to that of the other illustrated IDBs for which the relative reliability score will be lower.

In fact, in this very simplified illustrative embodiment, the IDS for individual A 340-A and the IDS for individual B 340-B will include a main data record for individuals A and B which will include personal identifiers verified from two different sources. In addition, the IDS of individual A 340-A. for example, will also include relationship data on individuals B, C and D. However, as individuals C and F are related to individual B they may also be included as relationship data in the IDS of individual B 340-B.

In the case of a plurality of users entering IDBs, an IDS may be generated and may receive verification from a large number of sources.

Reference is now being made to FIG. 5 which exemplifies the comparing of data bits on an individual obtained from two different IDBs. Illustrated are data bits on individual A which are included in the IDBs inputted by User-A and in the IDBs inputted by User-B.

Often data bits on an individual entered from one source may include inaccuracies or may be incomplete. As is illustrated in the example of FIG. 5, 9 different parameters on individual A are included. User-A has inputted data relating to his/her age, gender, place of birth, eye color, date of birth, father's name, mother's name, brother's name and residence ($A_1$ to $A_9$, respectively). User-B has inputted corresponding data relating to User-A, save for bits $A_8$ and $A_9$. In some embodiments, the two sets of data bits are compared to provide a binary output of "match/mismatch" ("YES"/"NO"), relating to the two pieces of data that were compared. A more complex algorithm may be applied upon comparing of pieces of data on the same individual from multiple IDBs. In some other embodiments, the output may provide a score based on the closeness of match. For example, relating to the data in FIG. 5, if a binary scoring system is used then the father's name of User-A will be accepted (as both inputs match and are "Peter") and if a score is provided, such as ten out of ten. In contrast, if the binary comparison system is used relating to the mother's name, the input will be rejected as "Mary" and "Marie" do not match, whereas, on a scoring basis, the score may be eight out of ten. Similarly, the age of user$_{(I)}$ may be rejected on a binary basis, but ascribed a score of 9 on a scoring basis. Regarding the place of birth, if a binary comparison system is used, then "Baltimore" and New York" do not match, whereas on a score system, a score of 4 out of 10, for example, may be provided. For brother name and residence, no data is provided in the IDBs of User-B and while in a binary comparison system this data may be rejected, in a scoring system this may receive a medium score such as 5. In the subsequent constructed IDS, in the case of the binary system, the data bits to be entered may include only those with a full match. Against this in a scoring system the data to be included may be such with a score above a certain number, e.g. a score greater than 5, in which case data bits $A_1$, $A_2$, $A_4$, $A_5$, $A_6$ and $A_7$ will be included. Furthermore, the IDS may be ascribed a total reliability score based on the individuals score a typically also factoring in other factors such as the number of IDBs used to construct the IDS, the number of related individuals, the reliability score of related individuals, etc.

In some embodiments, different weightings may be given to different data bits. For example, the weighting of data provided by an individual regarding himself may be twice that of a sibling relating to that individual and three times more than that received from a cousin regarding that individual. The degree of closeness of the user providing the information relating to the individual may be used to calculate the weighting. The weighting may therefore, for example, be calculated as a function of the number of verifications multiplied by the weighting assigned to each of the verifications (each of which is itself a function of the closeness of the two users in that verification).

Thus, in some embodiments the data provided by User-A regarding the mother's name, place of birth and age may be accepted, whereas these data provided by User-B may be rejected due to the lower weighting thereof.

It should be understood that many different other weighting models and comparison algorithms, including such that are known in the art, can be applied in accordance with the invention.

Figure 6A:
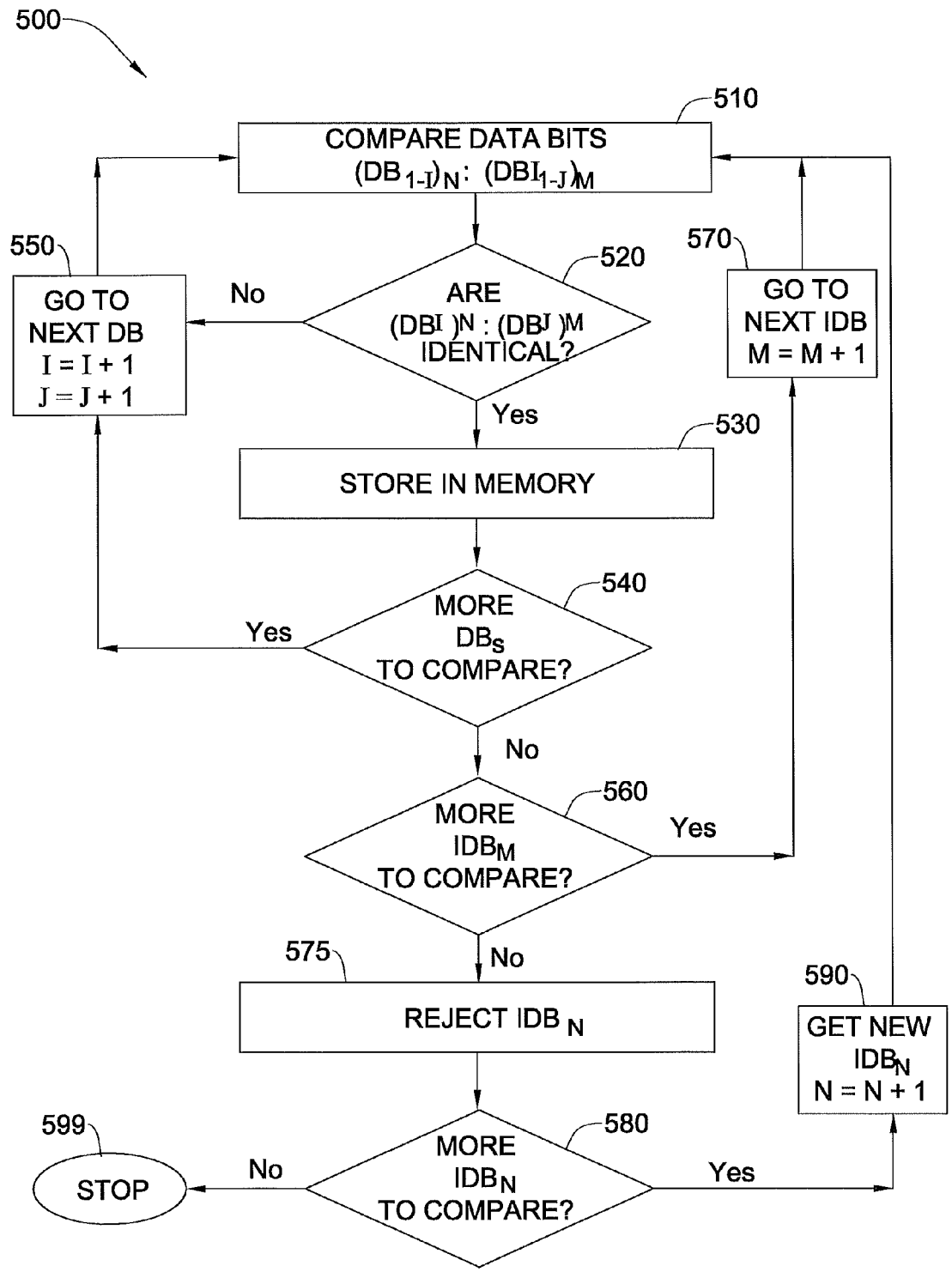
FIG. 6A is a simplified schematic flowchart illustrating an embodiment of step 320 of FIG. 4.

Reference is now made to FIG. 6A, which is a simplified schematic flowchart 500 illustrating an example of implementation of the processing step 320 of the embodiment of FIG. 4.

In a binary comparison step 510, the individual data bits in the IDBs of two users, User$_N$ and User$_M$ (data bits 1 to I of the IDB$_N$ of User$_N$, $(DB_{1-I})_N$, and data bits 1 to J of the IDB$_M$ of User$_M$, $(DB_{I-J})_M$), for example User-A and User-B of FIGS. 4 and 5, are compared. For example, the age of User$_N$ is compared to that provided by User$_M$ in the comparing step 510. As is seen in FIG. 6A, User-A has inputted her age to be 37, whereas User-B has indicated that the age of User-A is 38. In a checking step 520, the system checks to see if $((DB_J)_N$ and $(DB_J)_M)$ are identical. If the two data bits are identical, as in the case, for example, with respect to data bit A2 in FIG. 5, these data bits are stored 530 in the memory and then in a subsequent step 540 the system determines whether there are more data bits in the two IDBs to compare and if positive next data bits are selected 550 in the two IDBs and processes begins again. In case the comparison step 520 yields a negative result, the system proceeds directly to determining step 540.

In case the determining step 540 concludes that there are no more data bits in the two IDBs to compare, the system determines whether there are more IDB$_M$S to compare. If positive the next IDB is chosen 570, the next IDB being chosen from either a random list of IDBs or from a list of IDBs predetermined to have a high probability of matching data bits with the data bits included in IDB$_N$.

Should comparison step 560 yield a negative result, the IDB$_N$ is rejected 575 and the system proceeds to next determining step 580 to determine whether there are more IDB$_N$S that should be compared to other IDBs. If in the affirmative, a new IDB$_N$ is obtained and the system returns to step 510. If there is no additional IDB$_N$ the operation stops 599.

In some other embodiments, the IDBs are stored and assigned reliability values. The reliability values may be accumulated for each user so as to ascribe to each user a general reliability value (GRV). The GRV may be used to choose selected users having relatively high GRVs for providing information to the system and for eliminating the less reliable users with lower GRVs.

Figure 6B:
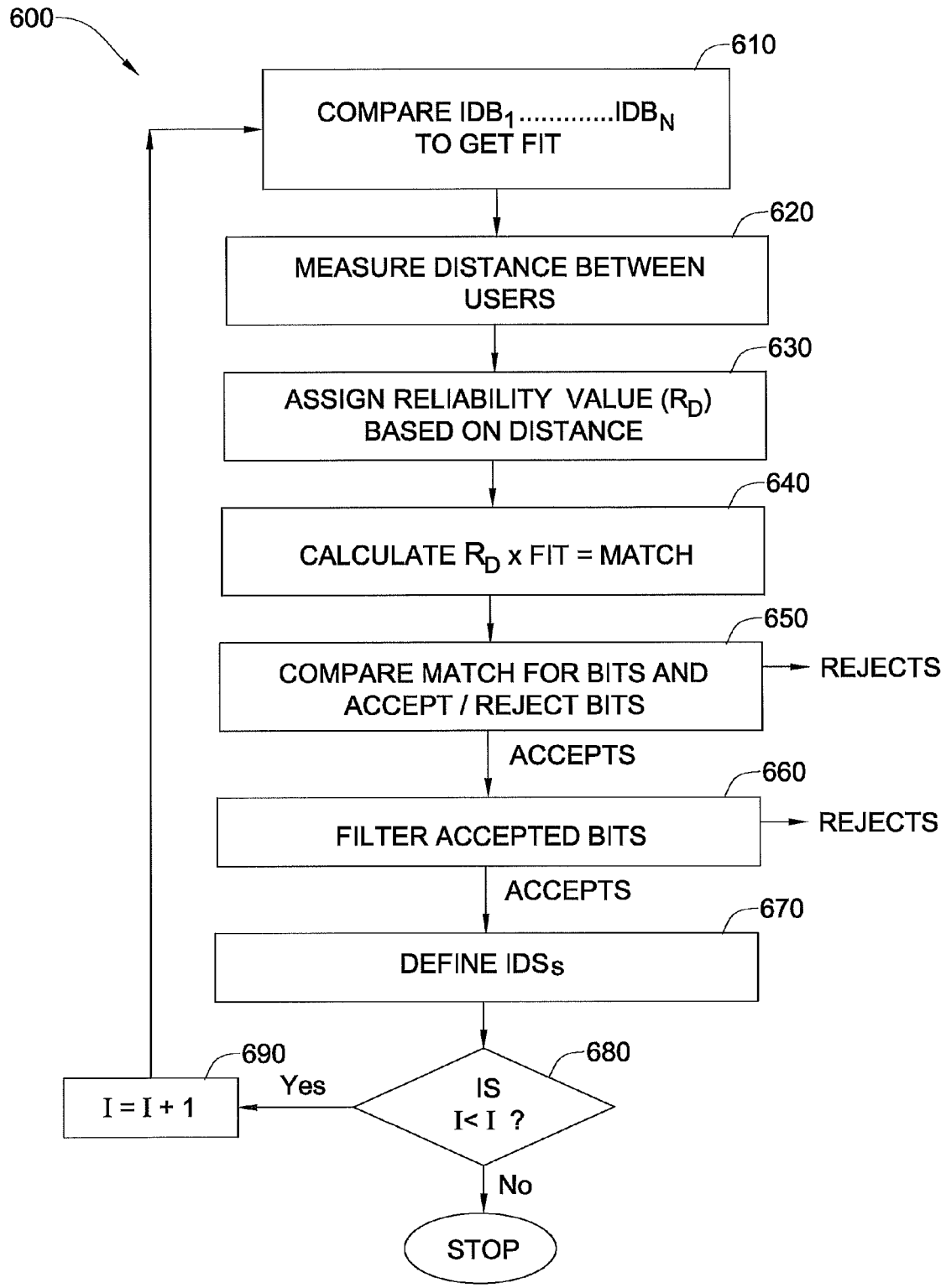
FIG. 6B is a simplified schematic flowchart illustrating an embodiment of step 120 of FIG. 1.

Reference is now made to FIG. 6B, which is a simplified schematic flowchart 600 illustrating an embodiment of step 120 for obtaining individual-identifier data set (IDS) of FIG. 1.

As is described hereinabove, and particularly with reference to FIGS. 1-6A, system 200 is operative to obtain IDBs for a plurality of users. The IDBs can be obtained over the internet and/or via any of the apparatus shown in FIG. 2 or any other known in the art. IDBs from different users are compared in flowchart 600. For example, the IDBs accepted in the illustrated example of FIG. 4, may be further compared taking into account the relative distances, namely the number of relationship lines, between the two or more users. In some embodiments, this is a further process in addition to the comparisons of IDBs made with reference to FIGS. 4-6A.

In other embodiments, this process at least partly replaces some of the steps described in FIGS. 4-6A. For example, in flowchart 600, the IDBs of multiple users designated IDB$_1$ . . . IDB$_N$ obtained respectively from users User$_1$ . . . User$_N$ are compared in comparison step 610. These IDBs may be pieces of information provided by a user regarding himself and one or more other relevant individual. When a comparison of multiple sources of data is employed in step 610, one or more algorithms may be applied to eliminate any extraneous data processing (such as by rational design methods, known in the art).

For example, in step 610, the IDBs obtained from a plurality of users relating to various identifiers can be compared to obtain a set of relative fits of the various IDBs.

The output of step 610 may include at least one of the following;
   a) a fit of IDBs obtained relative to data in a memory or database;
   b) a fit of IDBs obtained from one or more users relative to one or more other users;
   c) a plurality of IDBs pertaining to different users;
   d) at least one indication of a relationship and/or distance between two or more users.

In a measuring step 620, the distance between two or more users is calculated or measured. Distance may be defined according to one or more set of rules. One none-limiting example includes at least one of the following:
   a) A relationship line between two blood relatives of a first degree is standardized to one standard length away (such as a user to his child, parent, sibling or spouse); a line of two standard relationship lines may be standardized by a blood relationship of two degrees (such as a user to his grandparent or grandchild, first cousin, niece or nephew, sibling-in-law, parent-in-law) etc.; and
   b) A line between friends may be defined in relative terms of, for example: a lover, first degree; best friend, first degree (one standard distance away); social group friend, second degree (two standard distances away), work acquaintance, third degree (three standard distances away).

The distance between at least some of the set of users may be calculated using the one or more set of rules and outputted. Thereafter, the calculated distances are stored in the system's computerized memory.

In an assigning reliability step 630, the reliability of data obtained from a user concerning another user is calculated as a function of the distance between them calculated from step 620. For example, blood relatives of three relative lengths away, may be assigned a higher reliability value (to be designated herein as "$R_D$ value" or "$R_D$") than friends of the same relative length away.

In a calculating match step 640, the match is calculated as a function of the $R_D$ value. In some cases, this may be a simple multiplication of match using the corresponding fit from step 610.

In an accepting step 650, all IDBs having a match of more than a pre-determined value are accepted and others rejected. In some embodiments, only the accepted IDBs are saved to memory.

In an optional filtering step 660, one or more algorithms are applied to the accepted IDBs. The filtering step is designed to reduce the number of IDBs to a minimum and to reject "non-essential IDBs".

As already noted above, each IDB includes personal identifiers of the data-entering individual as well as data on related individuals. At the end of the process 670, an IDS, is defined for each of the identified individuals, which include the data-entering individual a well as the related individuals.

In a user checking step 680, it is checked to see if an IDS has been calculated for all of the identified individuals in all of the IDBs. If negative, a search is performed to find the next IDB in an update step 690 and then steps 610-680 are repeated until each of the identified individuals has a corresponding IDS. The IDSs are stored in the system memory 288.

The methods of the present invention for forming relationship webs are exemplified by, but not limited to the following example.

Figure 7A:
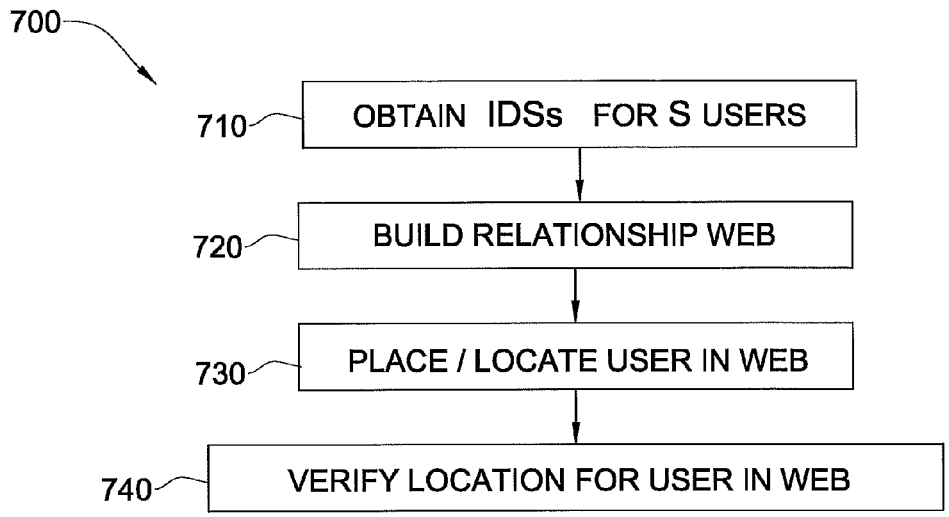
FIG. 7A is a simplified schematic flowchart illustrating an embodiment of step 130 of FIG. 1.

Reference is now made to FIG. 7A, which is a simplified schematic flowchart 700 for developing a relationship web, illustrating an embodiment of step 130 of FIG. 1.

In an IDS obtaining step 710, the IDSs of S users are obtained. This step may be similar to or different from flowchart 600 of FIG. 6B. In some cases, the IDS of some users are stored in one database and others in another database. The databases may be merged, or combined into a third database in system 200.

The construction of an IDS should be understood in the virtual sense in the generation of an ensemble of data which serves as personal identifiers of an identified individual and his related individuals. In accordance with one embodiment, all components which constitute one IDS are stored as one data record. In accordance with other embodiments, a plurality of elements constituting a single IDS may be distributed between a plurality of data records.

In step 720 a relationship web, as described hereinabove, is created, for example on the basis of the obtained IDSs. This can include creating family trees, creating society hierarchical trees, creating work hierarchical trees, and the like. According to some embodiments of the invention, isolated relationship webs are created for each individual, showing all individuals having a certain predetermined number of relationship links to that individual. In accordance with other embodiments of the invention, the relationship web includes a plurality of individuals, e.g. all individuals residing in a geographical location, all individuals of a defined religion or sect, all individuals belonging to a certain culture, and occasionally all individuals in the database.

One exemplary use of the invention is in the automatic construction of a family tree. Unlike many systems that permit a user to produce his family tree, in accordance with the invention the generation process is in fact automatic. Although the user enters some of the relevant data, other data relevant for the construction of a family tree for a specific individual may be entered by others, as is explained with reference to FIG. 5. Another unique feature of the invention that is permits merging of different family tree databases to one another.

Figure 7B:
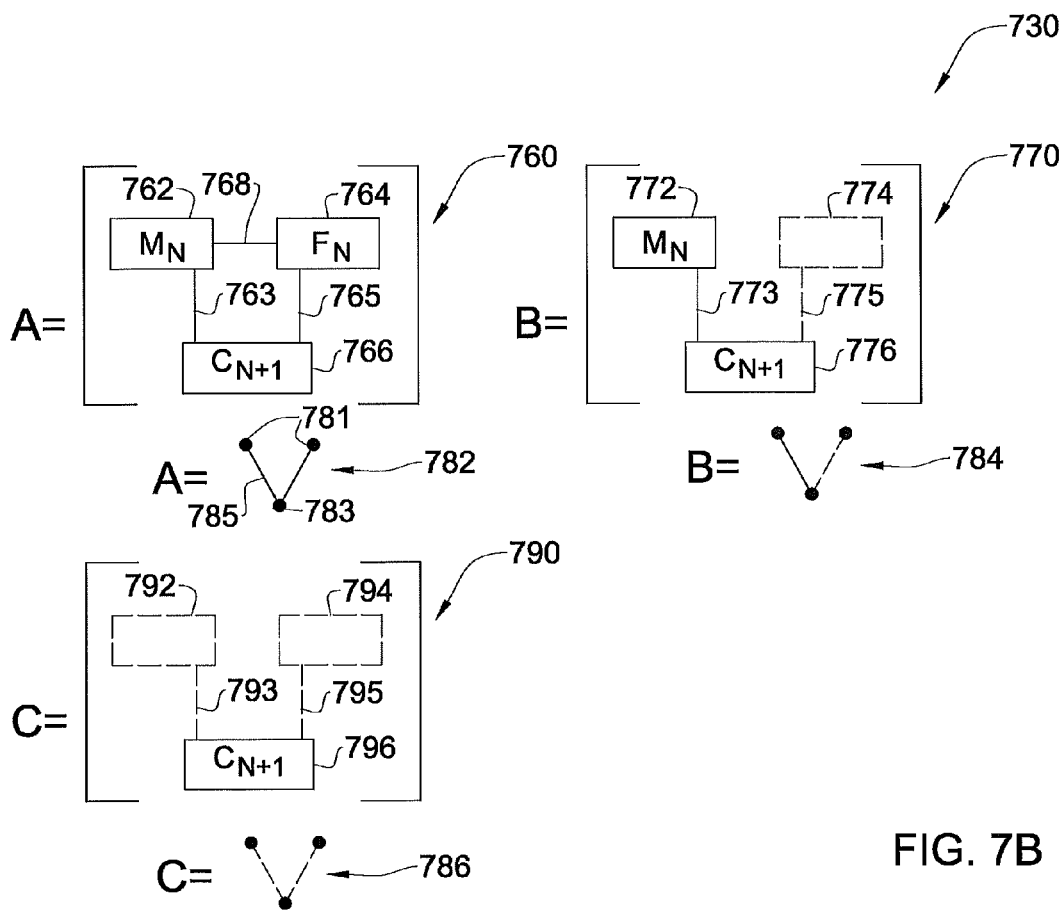
FIG. 7B is a simplified schematic illustration showing family structures and corresponding symbols, in accordance with an embodiment of the present invention.

FIG. 7B exemplifies family structures 760, 770, 790, in accordance with an embodiment of the present invention.

In accordance with some embodiments, each family or group of individuals can be provided with a family structure A, B or C. Family A represented by structure 760, has a mother 762, father 764 and child 766. The father and mother belong to generation N and the child to generation N+1. There may, of course, be a plurality of children (not shown). The mother and father are linked to the child with one line each 763 and 765. If married, the mother and father are linked with line 768.

In family B, represented by a one-parent family comprising structure 770, the father is (currently) unknown. The mother 772 is linked to child 776 by a solid line 773. The father 774 is linked to the child by a dotted line 775.

In some other cases, such as in family C, represented by structure 790, there are no known parents. Child 796 is linked to mother 792 and to father 794 by two dotted lines 793, 795 respectively.

The family structures of A, B and C may be denoted in "shorthand" as 782, 784 and 786 respectively, as is shown in FIG. 7B, where the child related node is denoted 783, and the parents' related nodes—781 and 782 respectively.

These families may be real genetic families or families of people who have a certain social or work relationship.

Turning back to FIG. 7A, the building of the relationship web utilizes creation of the family tree. The family units are sorted and categorized. Thereafter, they are compared and super-imposed so as to form one or more relationship webs with a proper location of each individual therein (step 730). In some cases, steps 720 and 730 may be combined or their order reversed. For example, the construction of the relationship web may comprise a combination of placing individuals and families within a web.

In some embodiments, the relationship web is formed by combining a plurality of family structures, particularly family trees, included in two or more IDSs. As already noted above, each IDS includes, among others, personal identifiers and relationship data on related individuals. Thus, as also already pointed out above, each IDS constitutes a sort of a family database and may be used for construction of a family tree. By combining relationship data included in different IDSs one family tree may be enlarged and merged to others.

Data included in an IDS is already verified through some mode of verification, particularly such IDSs constructed from IDBs entered by a plurality of individuals. Thus, data included in an IDS will have some degree of verification whereby each related individual included in an IDS is already a verified individual and accordingly family trees merged in that manner are verified family trees.

As already pointed out above, while an IDS contains data on related individuals, at the same time there is also an IDS for each of the related individuals. Thus, upon merging of family trees through association of family databases from two or a plurality of IDSs, all IDSs associated with their related individuals in the IDSs which constitute the basis for merger may be updated, automatically, for example, by addition of related individuals to such IDSs as a result of new individuals who now become related through such merger of family trees.

Figure 8:
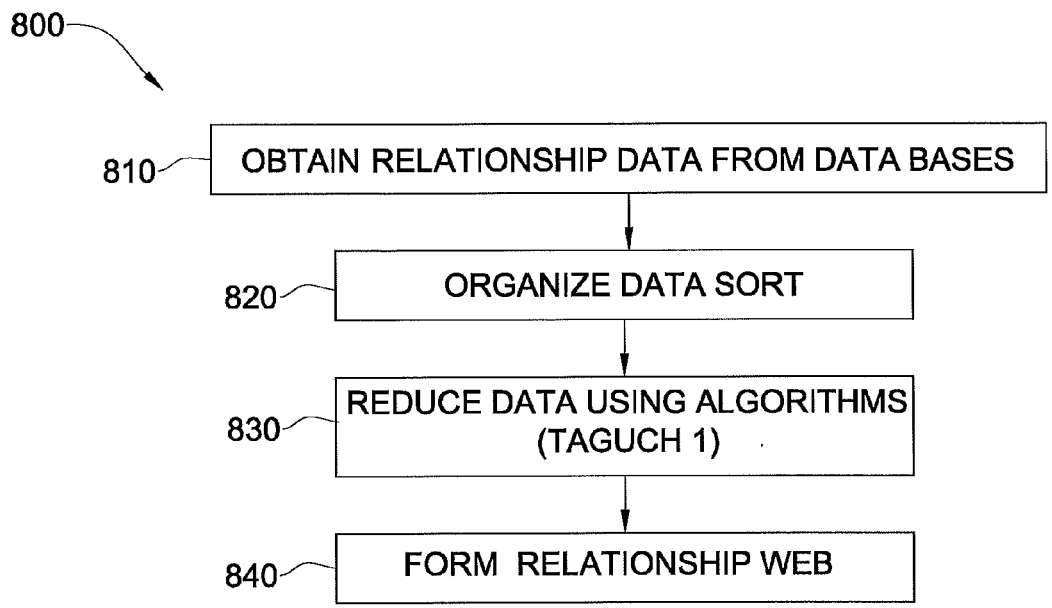
FIG. 8 is a simplified schematic flowchart illustrating an embodiment of step 720 of FIG. 7A.

Reference is now made to FIG. 8, which is a simplified schematic flowchart 800 exemplifying the formation of a relationship web (step 720 in FIG. 7A).

In an obtaining step 810, data regarding an individual is obtained. The so obtained data may be sorted according to a number of different parameters such as, but not limited to, type and relative position (step 820). For example, data may be sorted into the type of relationship web, family, friend, work etc. The data may be sorted according to relative position, for example, age, generation, geographical location and sub-location.

In a data reduction step 830, the quantity of data regarding the individual is sifted using at least one algorithm, such as by rationally designing the required data set, as is known in the art. In some embodiments, this step may precede step 820 (the data is sifted before sorting), in some other embodiments (as shown in the figure), sifting is applied to the sorted data.

The reduced data is then processed to form a relationship web (step 840). For example, a relationship web may be formed by combining a plurality of family structures (such as 782, 784, 786 of FIG. 7B). The relationship web may typically have a multidimensional topology.

The data obtained in the previous step may then be used to associate individuals, including, but not limited, individuals belonging to a single family, in a relationship structure one versus the other. In some cases, an individual may appear in several different family structures, such as family trees. Such an individual can then be used as a reference point to connect between the different structures and/or family trees.

The methods of the present invention for verifying relative positions on relationship webs include, but are not limited to standard vector matching methods. Using algorithms known in the art, the reference points between different structures/family trees can be ascertained with a very high degree of probability.

Figure 9:
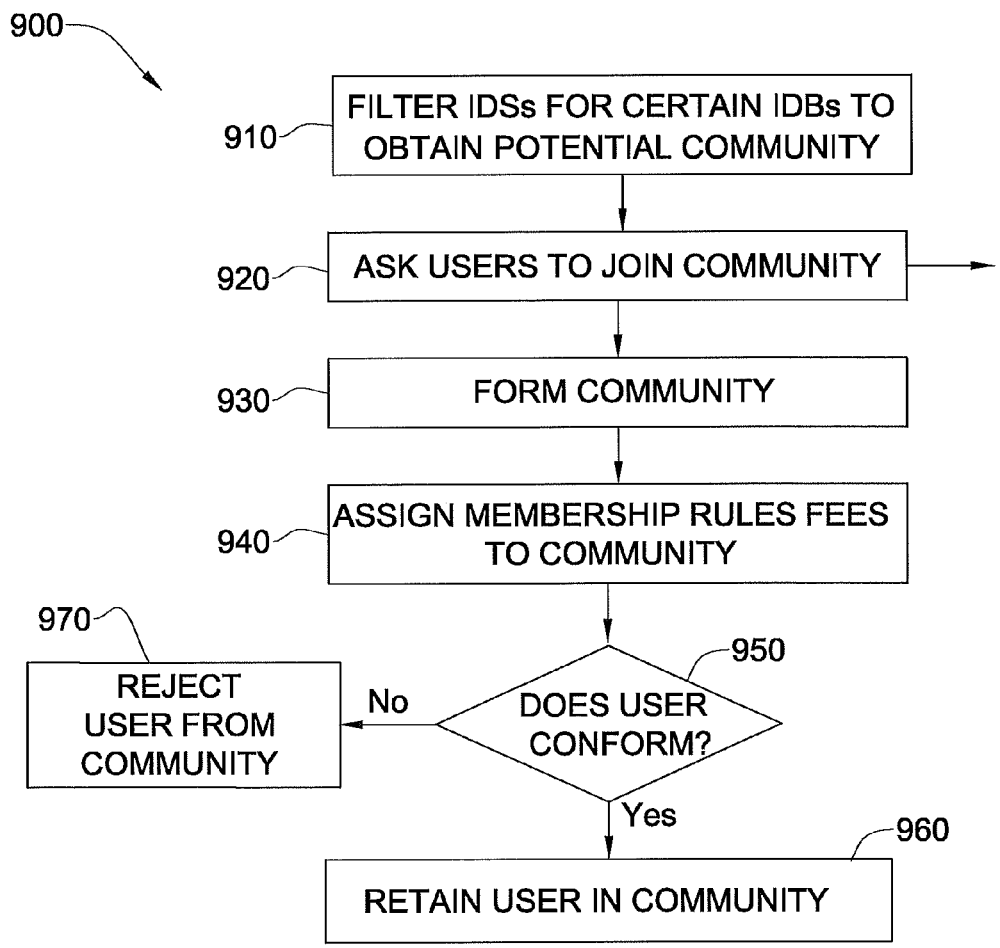
FIG. 9 is a simplified schematic flowchart illustrating an embodiment of step 140 of FIG. 1.

Reference is made to FIG. 9, which is a simplified schematic flowchart 900 exemplifying formation of a virtual community according to embodiment of FIG. 1.

In a first filtering step 910, the IDSs obtained in step 130 of FIG. 1 are filtered, for example, with regard to one or more indicators such as residence, scope of interest, hobby, demographic parameters, and others. For example, cyclists in the Regent's Park area in London, UK, can be selected in this manner from all other individuals.

In a subsequent asking step 920, all such selected individuals may be asked, by the system, if they wish to join a "Regent's Park Cycling Community". Of those asked, some may provide a positive reply by, for example, following a link which links them to a web page within the system website, that is formed for the "Regent's Park Cycling Community". A membership list of such formed virtual community may then be drawn and may be made available to all the identified individuals who chose to join this virtual community.

In an assigning rules and fees step 940, the joining individuals are asked to pay a standard annual fee and to agree to abide by a set of rules. For example, the rules may include: a) paying the fee by April of each year, b) not riding on the pavement (sidewalk) in London, c) not riding within 50 meters of the Regent's Park mosque unless fully covered, d) always using a front and rear lamp from sunset to 8 am; and e) applying a membership sticker to the front handlebars of the bicycle so as to be easily identified.

In a checking step, 950, the joining individuals if the abide by the rules. If, for example, the user does not pay the annual fee by April, he may be rejected from the community. Likewise, he may be rejected if he is found to break any of the rules b) to e). If he conforms to the rules, he is retained within the community until the April of the subsequent year.

The method as exemplified herein enables the formation of a database in which the reliability of the IDSs are high and the probability of the verified data being incorrect is low. Furthermore, the superimposition of the family structures as shown in FIG. 7B provide a verification of identity tool superior in reliability to any other tool known in the art heretofore. The identity of an individual is verified by the methods of the present invention with a high degree of probability. Furthermore, the relationship between different family members is also verified unequivocally. Thus, the databases formed using the methods of the present invention may be used for many applications, as are exemplified herein.

The IDS containing databases of the invention contain verified data on individual and their relationships. Such databases may be used, in accordance with the invention, for a variety of uses where verification of user's identity is important. Such may include, for example, a variety of applications in internet e-commerce, for virtual networking with real and identified individuals, etc. Some applications that make use of the verified data included in the database of the invention will be exemplified further below. The fact that the IDSs containing database of the invention includes real and verified information on the individual's and individual demographics, may be used for a variety of uses for which computer network have not been used hitherto. Such may include, for example, demographic research, opinion polls, referenda and elections.

For example, demographic surveys and opinion polls can be carried out, on the basis of gender, age, ethnic type, religion, nationality, social status, and generally any breakdown of parameters of the identified individuals. All such surveys and opinion polls may have a relatively high accuracy as the data in the IDS, and hence the breakdown of the individual into groups of individuals with identified parameters, is with a relatively high reliability.

Use of the database for marketing purposes, such as for targeted marketing to individual with selected personal identifiers, is another possible application of the invention. Such targeted marketing may be to individuals selected through certain personal identifiers, may be to a group of individuals belonging to a virtual community formed in accordance with the invention, typically such which relates to the interest focus of such a virtual community. For example, a computerized chess game may be marketed to a virtual community of chess players.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Since the relative position of family members are reliably mapped according to the present invention, the nearest scheme may be located which may be important, for example, for purposes of adoption of individuals to related individuals, in order to allow to claim an inherited estate of an heirless deceased, etc.

The following are some examples of uses of the database configured as described above.

EXAMPLE 1

Medical Applications of Family Tree Databases i) Blood Type

The blood type of a very large numbers of users/individuals may be known and verified using the individuals related database (main database including the IDSs all identified individuals and a relationship web. Thus, in this specific example, the blood type is a predetermined parameter for creating the verified database (227 in FIG. 3) and creating therefrom a sub-group database (229 in FIG. 3). This information can be used for obtaining blood from blood donors, for example.

Figure 10A:
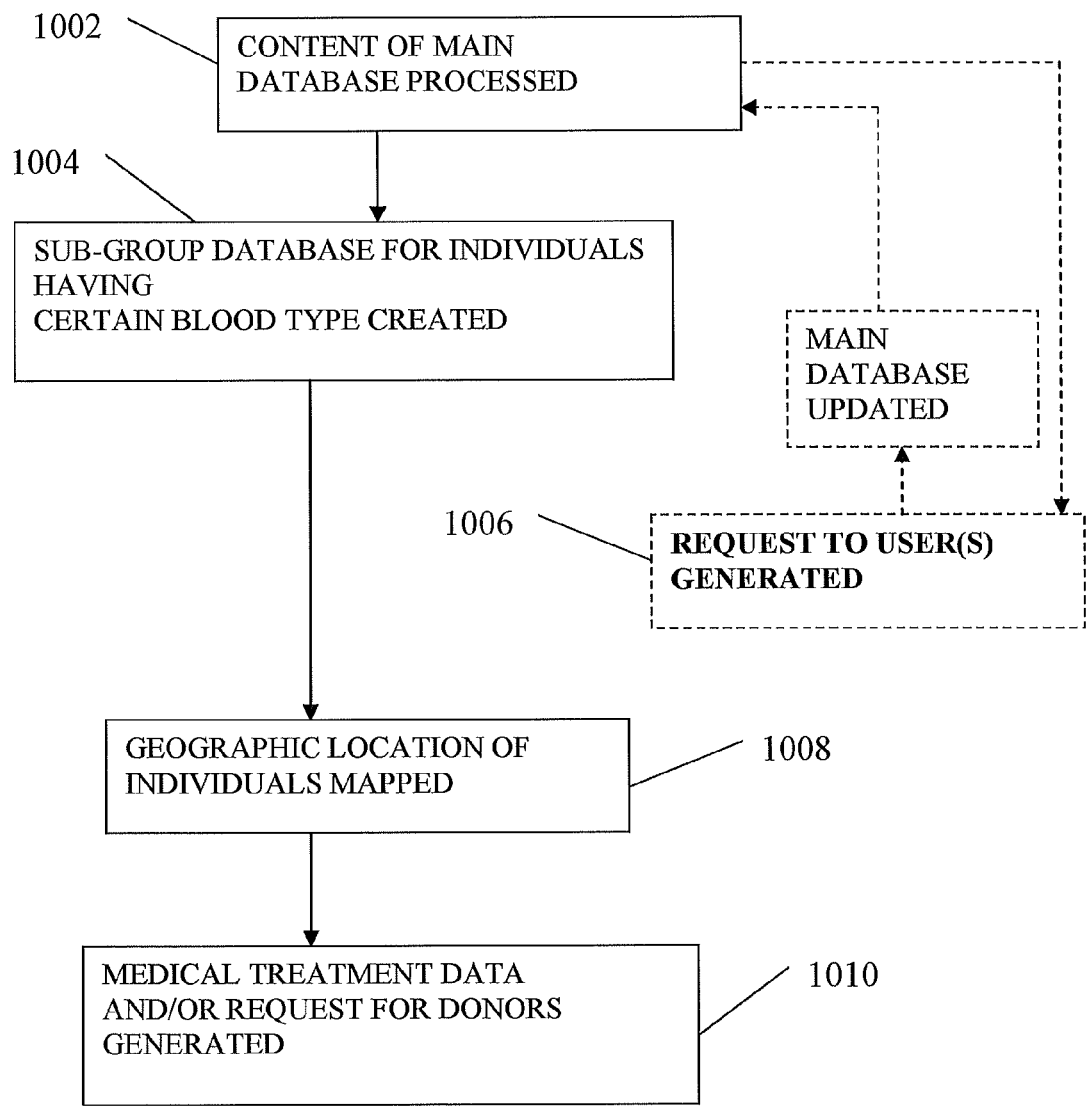
FIG. 10A is a simplified schematic flowchart illustrating a medical use of the database of FIG. 1.

Reference is now made to FIG. 10A, which is a simplified schematic flowchart 1000 illustrating a medical use of the database created according to the embodiments of the invention.

In a first step 1002, a verified database (227 of FIG. 3) created as described above with reference to FIGS. 1 and 2 is processed to select those users' data records which contain blood type related data in order to further filter (by processor 228) the verified database to find individuals having a specific blood type, e.g. an AB-blood type, which is relatively rare (around 1% of the general population) and to thereby create a respective sub-group database. The verified database 227 is analyzed (by processor 226) and it may be found, for example, that of all the verified individuals in database 227, only 0.001% of the population are known to have the AB-blood type. This may mean that the data pertaining to blood type is absent in the main database for many of the identified individuals. In such a case processor 226 operates processor 228 to generate a request from all the residual 99.999% of the verified individuals information regarding their blood type or the blood type of their relatives and acquaintances known to them (step 1006). In this way a subgroup database 229 may be further updated.

Processor 228 (FIG. 3) may be configured to map all of the population in the sub-group database having the AB- blood group according to their geographic location (step 1008).

In a provision step 1010, for example, the individuals of the sub-group identified as living in Greenwich Village, New York having the AB-blood type may be invited to obtain a medical treatment, a diet related to blood type, or asked to donate blood, due to a local shortage thereof.

If the blood type of a user is known, then the user can be advised of dangers pertaining to his/her specific blood type. For example, a woman of O− (Rhesus negative) can be warned of the dangers of becoming pregnant from an O+ (Rhesus positive) man and can additionally be provided with advice regarding immunizations before/during pregnancy.

A family having a certain blood disease, such as sickle cell anemia, thalessemia or hemophilia can be mapped to find disease carriers, to prevent marriages with increased predominance of the disease and to find diseased individual and to provide them with the correct therapy, such as gene therapy, if available.

Diets for a certain blood type known in the art may be marketed to individuals or families of that blood type, as those individuals or families have been mapped, according to some embodiments of the present invention, as having that blood type.

ii) Diseases in Individuals

An individual suffering from a certain disease or having a certain familial trait, may be prone to certain diseases, may be prone to age-related disorders, etc. Since the individual provides some information to the main users' related database, the information may be used to assist him in the control, prevention and treatment of his/her potential disease or disorder.

The database may be used to map all individuals in a certain geographical area suffering from the same disease or disorder. These individuals of this target group may be offered the same or different treatments and their progress over time may be monitored.

Additionally, the target group may be offered trips to a certain hospital specializing in treating migraines.

Figure 10B:
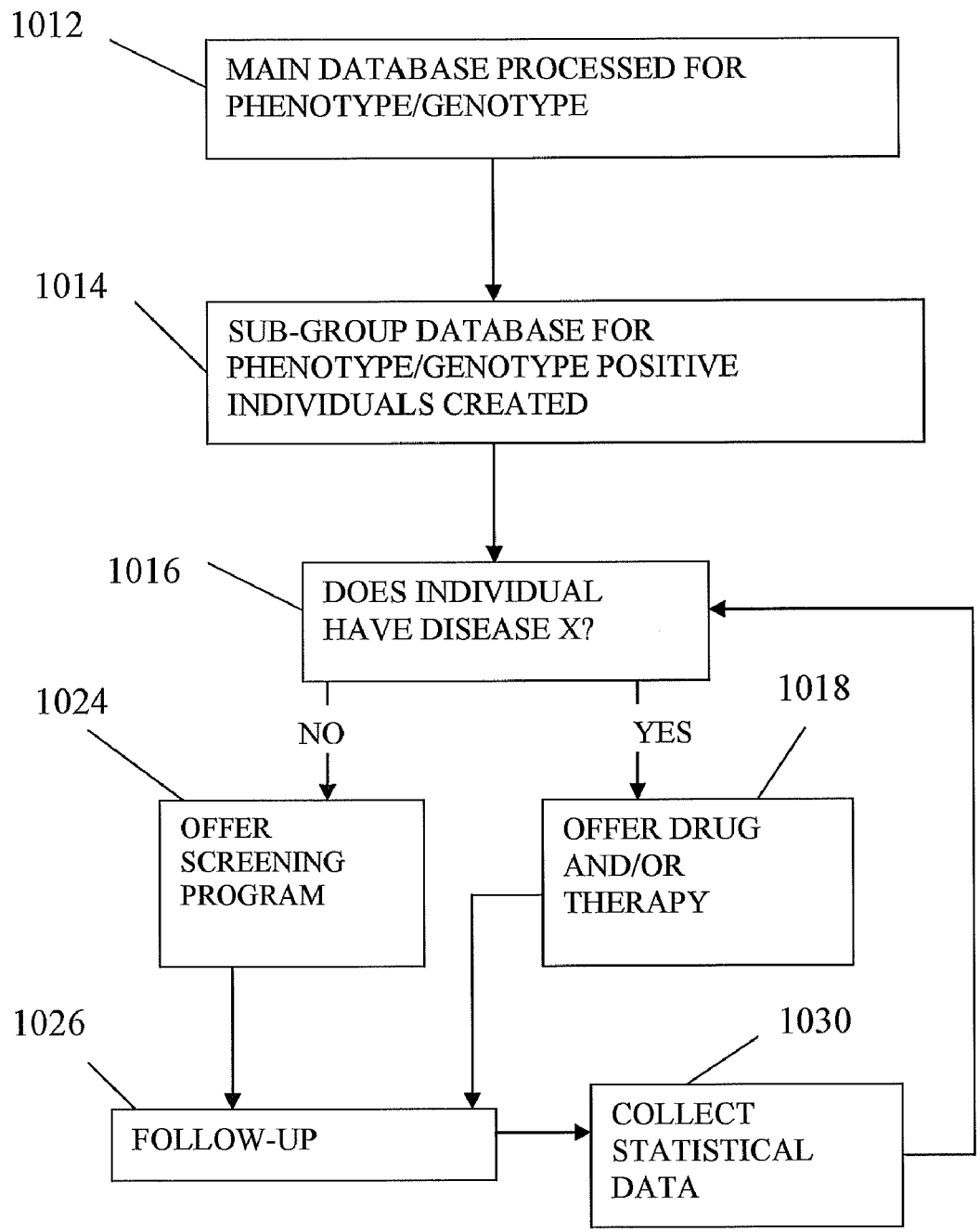
FIG. 10B is a simplified schematic flowchart illustrating a method for using the database of FIG. 1 for medical applications for a selected group of individuals.

Reference is now made to FIG. 10B, which is a simplified schematic flowchart illustrating another example of a method for using the users' related database for medical applications for a selected group of individuals.

In a processing step 1012, the main database is analyzed to select those individuals who have entered the relevant data into their data records or appropriately organize the data from the main database to find individuals who exhibit a certain trait, e.g. tyrosinase positive albinism and create a sub-group database of phenotype/genotype positive individuals (step 1014). It may be found for example, that of all the identified (verified) individuals in the main database, only 0.0007% of the population of the identified individuals are known to exhibit tyrosinase positive albinism (http://en.wikipedia.org/wiki/Albino). This may mean that the data pertaining to albinism is absent from the main database for many of the identified individuals. Thus, optionally, the respective request to the verified individuals can be generated and the sub-group database updated accordingly.

In a further processing step 1016, the sub-group database is processed to identify for each individual whether he/she has a disease or trait X. If YES, the respective individuals may be offered a drug and/or therapy (step 1018) and if NO a screening program may be periodically offered to the respective individuals (step 1024). The individuals may be followed-up (step 1026) and statistical data may be collected (step 1030).

iii) Diseases in Families and Community

Certain families have a greater incidence of certain diseases than that of the general population. These diseases can be divided into genetic diseases, such as a congenital heart disease, diabetes and non-genetic diseases, such as influenza, multiple sclerosis and various types of cancer.

Figure 10C:
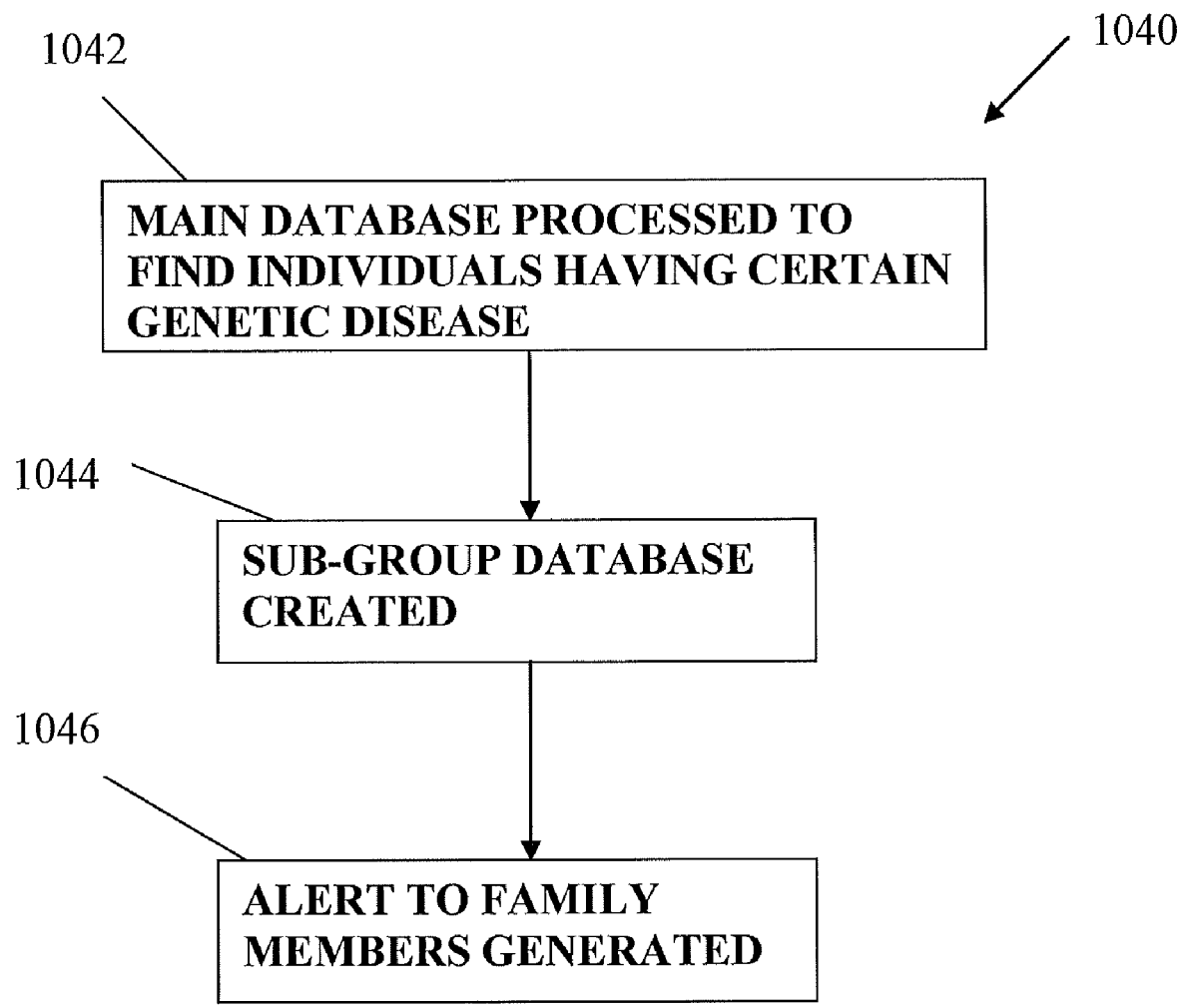
FIG. 10C is a simplified schematic flowchart illustrating a commercial method for using the database of FIG. 1 for medical applications for a selected group of individuals.

FIG. 10C is a simplified schematic flowchart 1040 illustrating a commercial method for using the database of FIG. 1 for medical applications for a selected group of individuals.

In a processing step 1042, main database is processed to find individuals having a certain genetic disease and a respective sub-group database is created (step 1044). Based on relationship data and/r generated family trees, family members of individuals having said disease are alerted for the possibility that they have such a disease and may be directed to perform necessary tests, go on a certain diet to reduce risk of having an active disease, such as in the case of Type II diabetes (step 1046). Optionally, such individuals may be offered certain drug-related information or other relevant health-related information relevant to them.

iv) Personalized Medicine

Although 99.9% of DNA shared among all people is identical, it is believed that crucial clues to health conditions are found in the slight genetic differences between individuals. It thus appears that family history may present itself as being one of the greatest risk factors for many diseases. Moreover, families share social and cultural traditions, behaviors and habits. These factors yield an immense impact on the overall health status of family members.

Personalized medicine may therefore be based upon both family medical histories and on a user profile.

Personalized medicine may be based on data/information from any one or more known family history initiatives including those of the Office of the Surgeon General; National Human Genome Research Institute (NHGRI); the Centers for Disease Control and Prevention (CDC); The Agency for Healthcare Research and Quality (AHRQ); and The Health Resources and Services Administration (HRSA). The data from these initiatives as well as using knowledge/data from policy makers (DC), researchers, insurers, providers, physicians, may be applied in conjunction with the database of the present invention to build a personalized medicine database. The data from the personalized medicine database may be used to analyze huge quantities of family-oriented health data. This personalized medicine database may be used for epidemiological studies over a period of time.

The personalized medicine database provides a unique ability to identify genealogical traits and personalized risk factors based on authenticated user family trees and associated family histories.

Based on the associated family history and other risk factors, a disease risk assessment can be performed, leading to a set of recommendations for one or more of: lifestyle changes to aid disease prevention; prescribing screening tests for early disease detection; recommending genetic tests for determining if any other family members are at risk; and, most importantly, family members may benefit, both directly and indirectly, from the database capability to accumulate huge amounts of authenticated family oriented health data. By "directly" is meant that the individual may be provided with real-time information regarding a disease from which he suffers, such as new drugs or clinical trials. By "indirectly" is meant that an individual may be provided with information which he can use to assist one or more of his known relatives.

The personalized medicine database may provide information or marketed products or therapies to individuals according to the individual's age, gender, health status, genetic status, socioeconomic group, genotype, phenotype, ethnic group and geographic location.

A young individual may wish to follow his growth rate, and thus the database may provide him with growth charts (height, weight etc.).

A middle-aged individual may be interested to monitor his cholesterol, LDL and HDL level and would thus be provided with charts to be filled in over time by his health practitioner.

The database normally comprises two classes of individuals: participating individuals (e.g. the family tree builder) and reported individuals (e.g. a late ancestor or a non-participating or passive family member). Each individual can belong either to one of the classes or to both of them. Thus a health form to be filled in by an individual may be a first or a third party report. In the second case a ranking algorithm which takes into account the number of identical reports and the genealogical distance of the reporter is used for evaluating the authenticity of the reported health condition.

Data, whether from a first, second or third party, may be entered manually into system 200, though may alternatively be retrieved from laboratory reports.

Additionally, an individual may be asked to provide data pertaining to his immunization history including active immunizations and as a result of disease.

The personalized medicine database may be used to provide a disease progression report and a progression graph.

Additionally, the personalized medicine database may be used to generate tables or charts of some of the data. The data may additionally be exported for use in risk assessment and actuarial analyses.

The technique of the present invention for creating the verified database allows users to map their individual world of family connections, creating a unique personal web which provides an authentic basis for understanding and carrying out interactions with family, friends and colleagues. The system may represent data, including a user's map of his personal world of family connections, in a layered form: each custom application corresponds to a certain facet of the user's real life, always utilizing the basic layer (e.g. geographic info, cultural and religious denomination, medical history, etc.) of genealogical connections. Practically, tailored applications and global family bonds empowered by sharing life experiences and information can be utilized. A user is allowed to merge a personal family tree with any and all other verified trees that are related to anyone on his original tree. As members are added and family trees are established and verified, the system begins identifying genealogical matches. Family trees begin to connect, global families grow and new relationships are discovered. The synergy of trees into forests creates a personal web of family connections and, in turn, interconnected data, which has not been previously available.

Figure 10D:
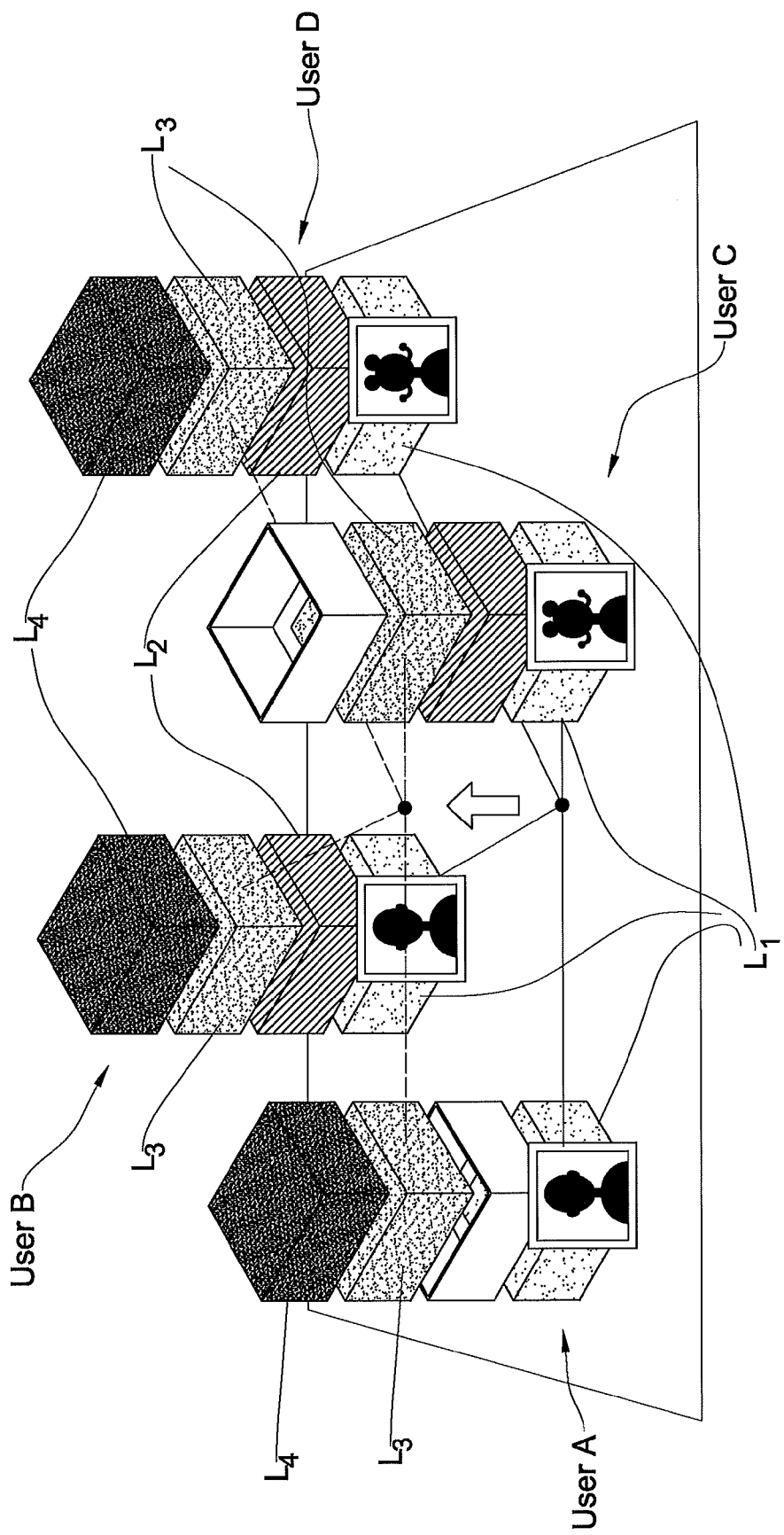
FIG. 10D exemplifies a layered structure of the verified database family tree including medical data records.

FIG. 10D exemplifies such a layered connectivity model. As shown, users A, B, C and D are associated with stacked pillars of independent layers of data. Here, $L_1$ is the basic connection layer, $L_2$ is the life style habit layer, $L_3$ is the personal medical history data layer, and $L_4$ is the third party dedicated service layer. As shown in the figure, the only data shared by default, in this example, is the basic connection layer. The data pieces of different layers are logically, and optionally physically, stored separately. The system operates to constantly mirror the relevant layers to the medical information providers. It should be noted that the system (through its gateway) may also relay information from one information provider to another, based on custom cooperation agreements.

Such layered approach to user data enables a secure and versatile model of data distribution, allowing each information provider full control over the collection of the dedicated user information. The only information that might be stored in the central system is the users' name and set of connections. In this manner, data collected by the individual medical information providers is instantly put into genealogical context, setting the infrastructure to powerful personal applications. The layered infrastructure will also allow medical services to correlate their medical records with the individual instances and links, and thus clinically harvest the user database. This feature represents a one-way query, without streaming any information out of the care-takers' private system.

The present invention provides for establishing and verifying family trees and finding matches between individuals in the merged family trees. The system can recognize these matches beyond the user's knowledge boundaries, discovering unknown connections. As people join and build their family trees, the system identifies genealogical matches. The trees begin to connect, the global family grows and relationships can be found between any two people in the system. Inputting the genetic maps of individuals, allows extremely complex interdisciplinary cross-references (e.g., creating a cardiovascular profile, based on scattered endocrinological evidence). At the same time, clinical research may be conducted in order to identify new 'incriminating' genetic patterns, thus developing new preemptive diagnostic and even therapeutic protocols. In other words, the invention provides for family tree reconstruction enabling, among other, to be used in a bioinformatics instrument.

Figure 10E:
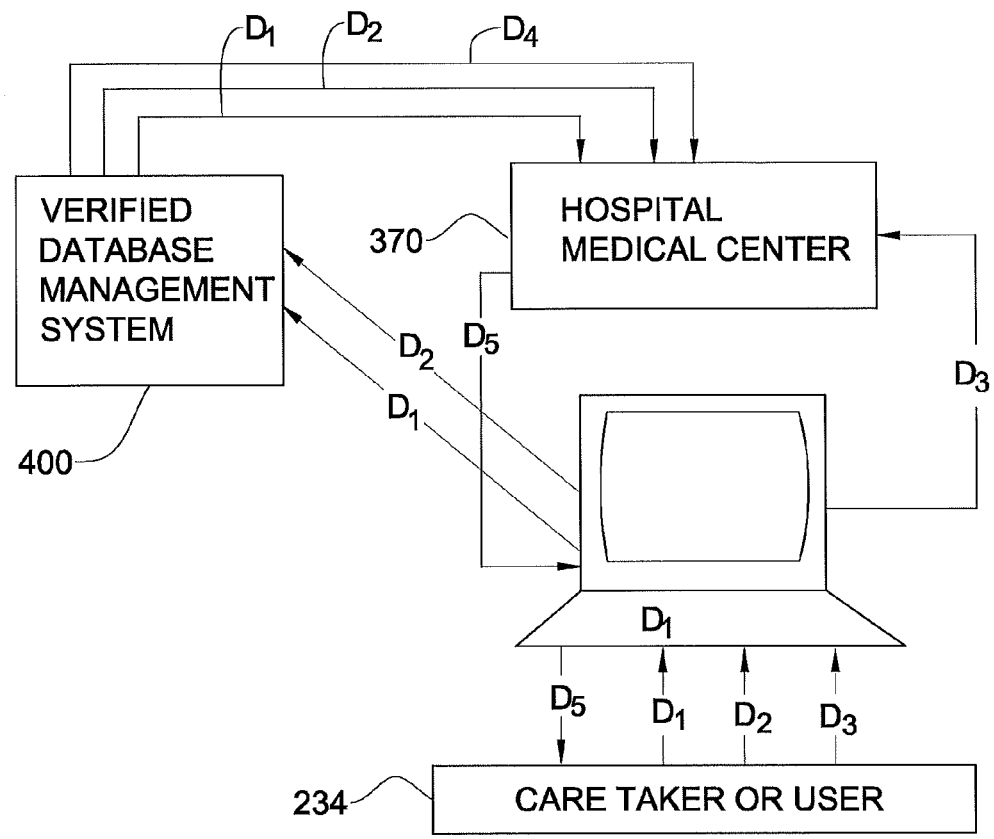
FIG. 10E exemplifies how the system of the present invention cooperates with a medical center to provide a user or care taker with a clinical profile, personalized information and custom services.

FIG. 10E exemplifies the data distribution between a care taker or user 234, the system of the present invention 400 (capable of processing data in the verified database according to one or more selected parameters or conditions) and a medical center 370. According to the layered connectivity model, all medical history information remains on the servers of the medical center and is controlled there. Lifestyle habits are mutually recorded, whereas all names and connections are mirrored to the system 400, under strict, mutually agreed upon, privacy protocols. Users are recorded in a layered fashion, as described above, from the very instance of individuals' sign up. As shown, a user or a care taker on his behalf, generally at 234, inputs, through his personal communication device connectable to the network, the user's pedigree $D_1$, life style habits $D_2$ and personal medical history $D_3$. The user's or care taker's communication device being either installed with a certain application program interface or operating according to instructions received from the system 400 via the network, operates to transmit these data pieces to the medical center 370, while the life-style habits and genealogical data $D_1$ and $D_2$ are mirrored to the servers 400. The latter generates a unified report of converged pedigree and life-style profiles $D_4$ and transmits this data to the medical center 370. At the medical center, the received data are processed to create personalized info and services data $D_5$ and transmit it to the user or care taker 234. The data piece $D_5$ may be maintained in the user-related data record in the database of the medical center.

Figure 10F:
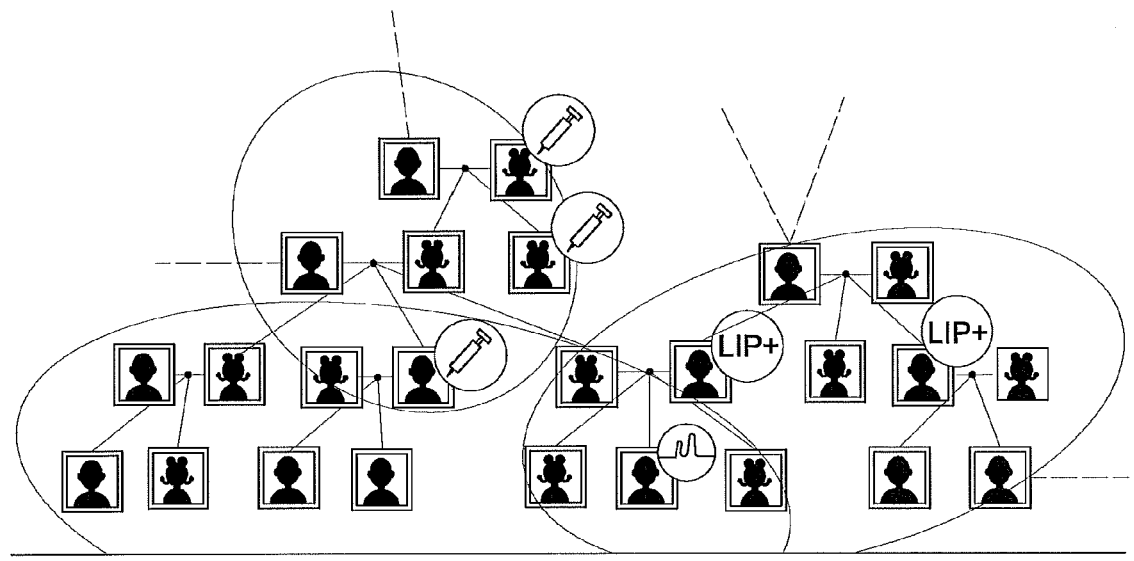
FIG. 10F is an exemplary illustration of merged family trees (each shaded area representing a separately created family tree that merged with the others), data on at least some individuals that includes medical information.

As indicated above, the technique of the present invention provides for a powerful proprietary convergence and management bioinformatics instrument. Using genealogical connectivity provided by the system of the present invention, user medical data can be converged with those of his/her entire authenticated family (pending each individual's authorization. As illustrated in FIG. 10F, connections reported from multiple sources converge and create an elaborate pedigree. The system performs the so-called "data mining", namely recognizes predispositions for diabetes and hyperlipidemia (both Endocrinological indications) and highlights the increased possibility for Ischemic heart disease (cardiovascular indication) among offspring.

v) Other Medical Applications

The database of the present invention may additionally be used to map drug resistance, drug allergies, drug-drug interactions, and drug-drug contra-indications. The database could be further used to prevent massive damage to large populations, such as in the "thalidomide" case. Such contra-indications could be mapped, according to certain embodiments of the present invention, in real-time, and the drug companies providing such a drug could be warned to stop providing it to users.

The database of the present invention could be used in gathering medical evidence and for suing drug companies on the basis of the gathered evidence.

Users may provide very detailed medical records to the database in order to receive good medical insurance and medical treatment package deals.

Figure 11:
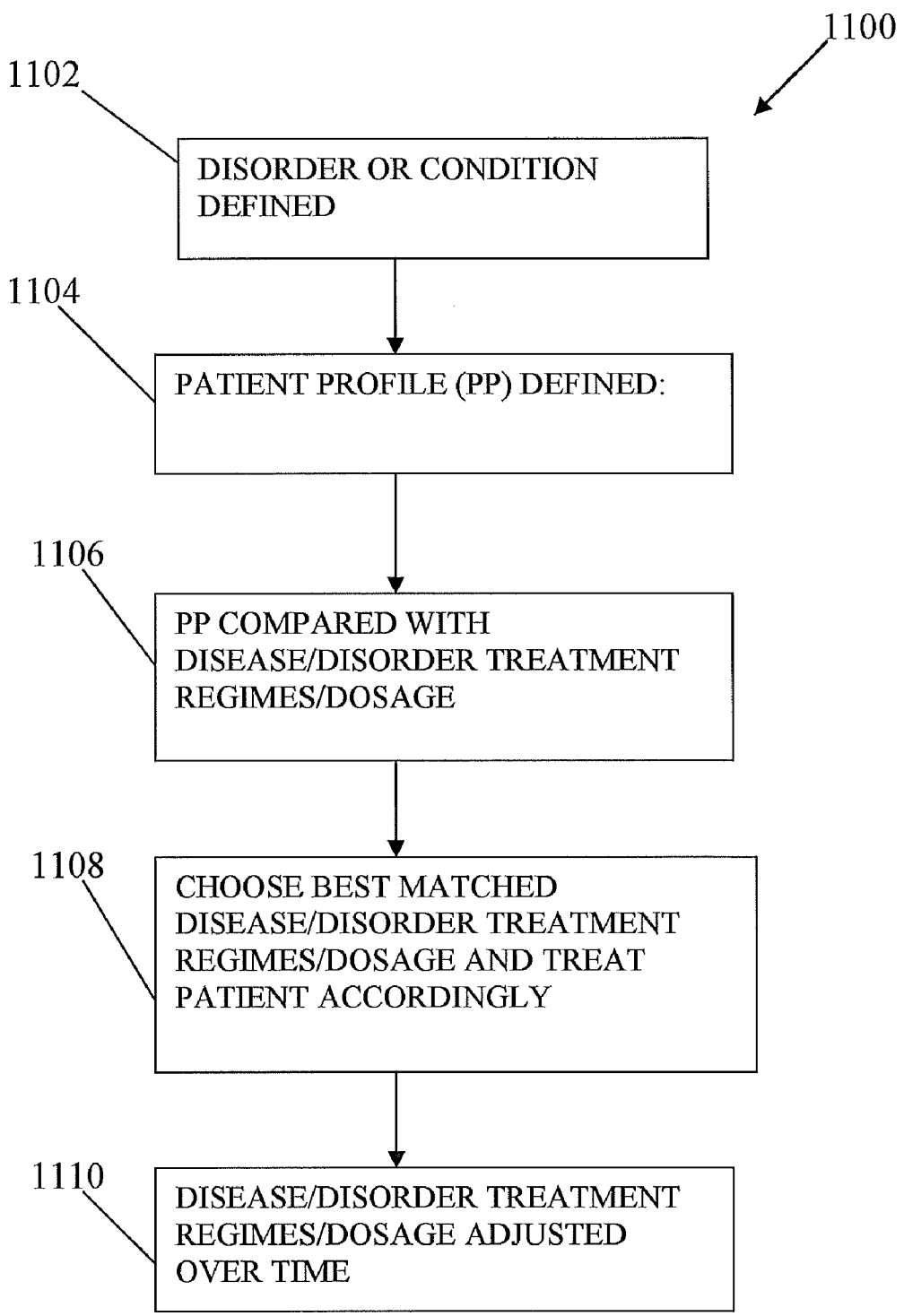
FIG. 11 is a simplified flowchart for providing a personalized medicine optimal dosage/dosage regimen of a drug, in accordance with an embodiment of the present invention.

FIG. 11 is a simplified flowchart 1100 for providing a personalized medicine optimal dosage/dosage regimen of a drug, in accordance with an embodiment of the present invention and operative using the systems described hereinabove.

In a first defining step 1102, a disease or disorder, which user/patient suffers from or is likely to suffer from in the future, is defined. This may for example be lung cancer.

Then, the personalized profile of the user/patient is defined (step 1104). The personalized profile may include, but is not limited to, any one or more of the following: personalized genetic profile (genotype, haplotype, place in the family tree created based on the verified database, family medical history); personalized medical records; age, location, socio-economic status, BMI; smoking and drug use profile; occupation; hobbies and other authenticated personalized data.

The personal profile (PP) of the user as defined in step 1104 is compared with the response of other patient(s) to known treatment regimes (e.g. using respective database 356 in the example of FIG. 3B)—step 1106. It is known in the art that some groups of individuals respond well to Gefinitib (Iressa) (see, for example, Sordella et al., Science 20 Aug. 2004: Vol. 305. no. 5687, pp. 1163-1167). If the genetic make-up of patient 234 is known, it can be used to predict whether a dosage is optimally matched to him. For example, if the patient carries a certain EGFR (Elongation growth factor receptor) mutation, then the patient may stand a better chance of responding to Gefinitib than persons not carrying the mutation.

Likewise, certain sub-populations respond better to a two drug therapy for lung cancer than others.

Thus in a choosing step 1108, the personalized profile of the patient, having been previously well defined genetically in step 1104, can be compared for matching with the known histories of patients in the same genetic sub-population(s).

The response to a treatment regime of the patient is monitored over time (e.g. using apparatus 390 in the example of FIG. 3B). Such monitoring apparatus feeds data to a tracking disease algorithms (362 in FIG. 3B). The treatment regime may be adjusted with time in step 1110 and data pertaining to the patient's state is further fed into respective database of the data managing system (e.g. system 350 in FIG. 3B). The patient's profile is updated accordingly in step 1104. This process may be performed for a large number of patients worldwide and the data used and compared to provide useful statistics which allow for improved adjustment of treatment regimes to one or more of the patients over time.

The database managing system of the present invention may therefore be used to provide personalized medicine to a very large number of patients worldwide, with both initial and updated optimized personalized dosage regimes responsive to each patient's initial and updated personalized profile, respectively.

In a similar way, the system may be used to predict the development of a disorder in a patient having a specific personalized profile over time. See, for example: http://clinicaltrials.gov/show/NCT00162435. This study shows that certain genotypes/haplotypes show very different responses to Warfarin over time. This means that one can predict morbidity in certain sub-populations over time. Thus, if the genotype/haplotype of the patient is known, one may consider whether warfarin is a good drug for treating the specific patient.

In the above-mentioned study, it was noted that the response to warfarin varies greatly among individuals. Some of this variability can be ascribed to genetic polymorphisms in the gene encoding for CYP2C9, the enzyme mediating the metabolism of S warfarin. In addition genetic polymorphism in other genes (i.e. VKORC1, factor VII) have been shown to account for some of the variability in the response to warfarin irrespective of CYP2C9. The present study has several segments:

Evaluation of the relationship between genetic polymorphisms in the genes encoding for CYP2C9, VKORC1 and factor VII and warfarin maintenance dose at steady state. This study is a confirmation of previous data in our own population.

Evaluation of relationship between genetic polymorphisms in the genes encoding for CYP2C9, VKORC1 and factor VII and warfarin loading dose during the induction period.

Testing the hypothesis that warfarin loading based on the individual's combined CYP2C9, VKORC1 and factor VII genotype may be more efficient and associated with reduced adverse drug effects.

Li et at. shows (J Med Genet. Published Online First: 12 Apr. 2006. doi:10.1136/jmg.2005.040410) that polymorphisms in the VKORC1 gene are strongly associated with warfarin dosage requirements in patients receiving anticoagulation These results are of considerable clinical interest and confirm recently published results regarding the role of these two genes in modifying warfarin metabolism and maintenance dosage. The consistent findings regarding the role of VKORC1 and CYP2C9 in warfarin metabolism and maintenance dosage represents a clinically useful proof-of-principal for the use of pharmacogenomic information in medicine and may lead to improved understanding of warfarin's actions.

Figure 12:
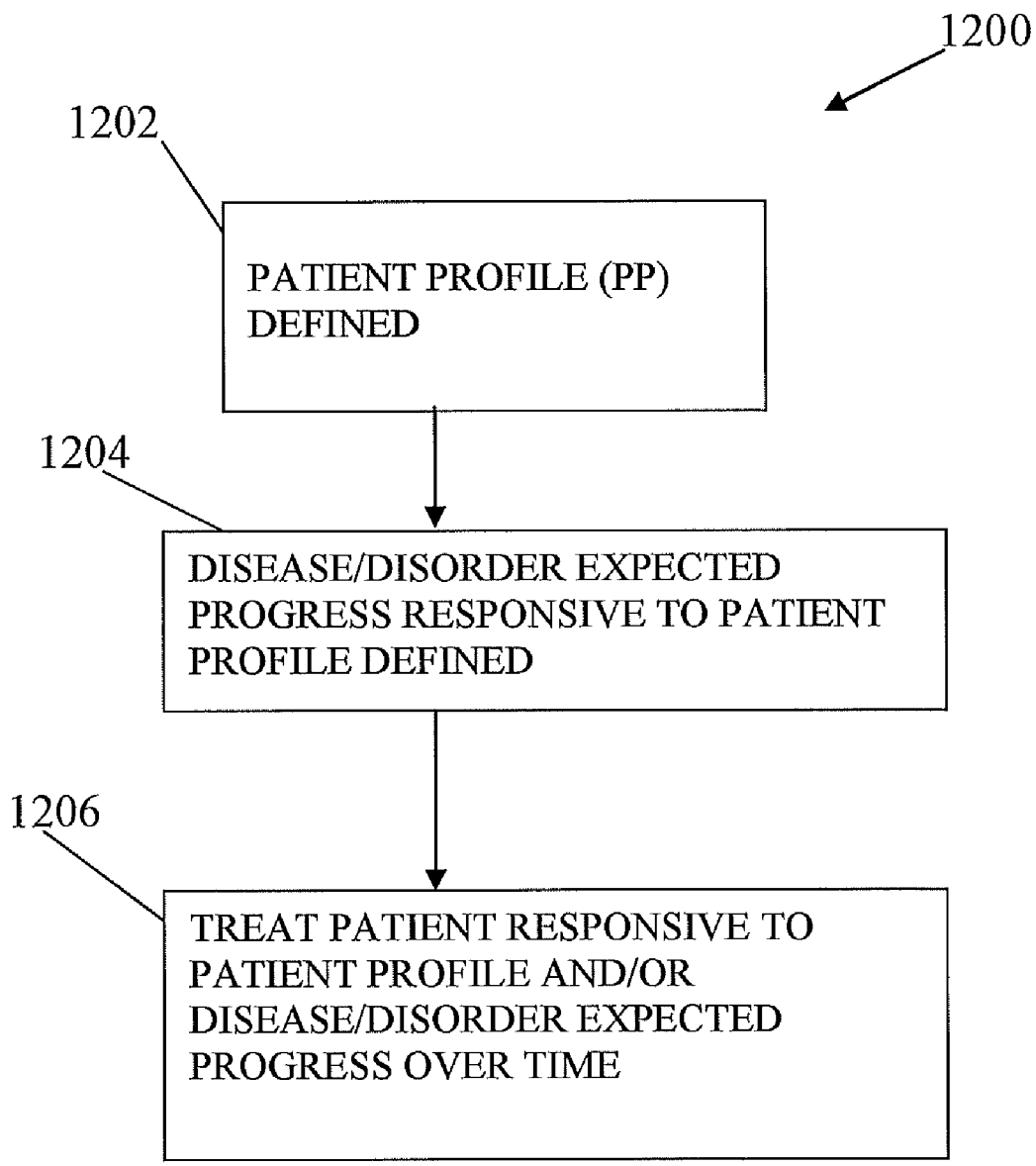
FIG. 12 is a simplified flowchart for providing a personalized medicine forward prediction of a disease or disorder, in accordance with an embodiment of the present invention.

Reference is now made to FIG. 12, which is a simplified flowchart 1200 for providing a personalized medicine forward prediction of a disease or disorder, in accordance with an embodiment of the present invention.

The profile of a user/patient is defined (step 1202). The personalized profile (PP) may include, but is not limited to, any one or more of the following: personalized genetic profile (genotype, haplotype, place in the family tree created based on the authenticated database, family medical history); personalized medical records; age, location, socio-economic status, BMI; smoking and drug use profile; occupation; hobbies and other authenticated personalized data; Allergies, etc.

A disease expected progress (DEP) is defined (step 1204). The progress of the disease may be predicted as a function of the patient profile. Thus, if the patient has a certain genetic profile, he may have an increased chance of morbidity relative to the general population. Alternatively, the opposite may hold true.

For example, it is known that Zarnestra (tipifarnib) targets proteins involved in signaling breast cancer cells to grow. Nearly one in four women on this drug in a phase II clinical trial had some sort of clinical benefit. In 76 women, Zarnesta (given in tablet form) produced a partial tumor reduction among 10-14% of the patients. In another 9-15% of patients, the cancer did not progress for at least 6 months. (bca.ns.ca/indice/2003/58index.cgi/noframes/read/229148)

In a treating step 1206, the patient may be treated responsive to at least one of PP and DEP. In other words, if his profile is known, he may be given a personalized dosage of one or more drugs, which is matched to the predicted disease progress (DEP) and or to his PP. This methodology should allow for improved individual treatment.

Figure 13:
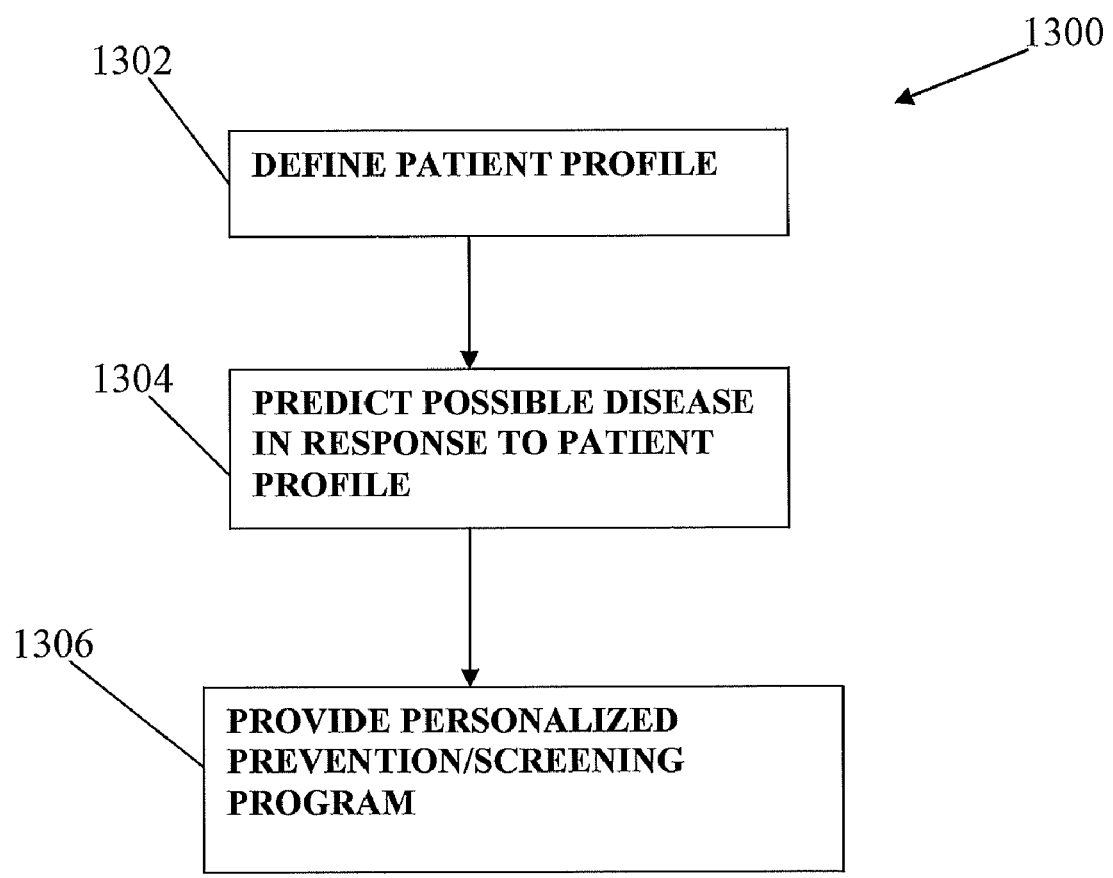
FIG. 13 is a simplified flowchart for providing a personalized preventative program to an individual, in accordance with an embodiment of the present invention.

Reference is now made to FIG. 13, which is a simplified flowchart 1300 for providing a personalized preventative program to a patient, in accordance with an embodiment of the present invention.

In a defining step 1302, the personalized profile (PP) of a user/patient is defined (as was described hereinabove with respect to FIGS. 11 and 12).

In a disease prediction step 1304, a respective processor utility of the system is operative to predict a possible disease (PD) responsive to PP. For example, a person with a history of heart disease in his family may be provided with statistics that show that he has a 30% change of a heart attack before the age of 60.

In a step for provision of a personalized screening/prevention program (PPSP) 1306, the patient may be routine checked for any subtle changes in his blood profile, ECG, BMI etc. He may also be provided with a prevention program such as a low dosage of aspirin to be taken daily from the age of 40 onwards.

EXAMPLE 2

Commercial Applications of Family Tree Databases

Many personal details pertaining to each user are verified by at least one other user and this feature of the present invention allows use of verified personal parameters. This holds true for both active and passive users. Active users are those who are in communication with system 200 and passive users are those who are reported by the active users, but are not themselves active users.

The data from the active users is used to form the database as described hereinabove. The database may be used to construct a global atlas and world people information bank. The global atlas and world people information bank may be used for analysis of data pertaining to sectors of the world community. The sectors may be defined according to any one or more of geographic location, age, gender, nationality, religion, lifestyle and socio-economic group. The sectors may be further defined according to profession, consumer habits, diet, health, fitness regime, membership of club, associations and guilds.

Thus, every person within the database may belong to several different sectors according to his personal profile. Accordingly, each sector or sub-sector may comprise a plurality of users who have several common denominators. Consequentially, the population of the sector or sub-sector may be targeted according to those specific common denominators. It should be understood that the applications exemplified herein of using the sub-sector comprising a plurality of users who have several common denominators for sectorial marketing should not be construed to be limiting. The present invention encompasses a very large number of possible applications of sectorial marketing.

a) Sectorial Marketing

Some embodiments of the present invention relate to targeted marketing to a sector or sub-sector of users according to their psychological, physical, spiritual and personalized characteristics.

For example, obese 18-25 year old males in the state of South Carolina may be offered a diet and psychological advice to fit their age group, ethnic group, weight, economic status and location.

For example, they may be offered a diet via a chain food store in that locality and a physical training program in some of the key cities. Due to the relatively low income of many of the people in that area, they will not be offered high-price sports equipment, nor ski holidays.

In contrast, obese 18-25 year old males who study in an Ivy League university may be offered a Weight-Watcher's program, high-price sports equipment and ski holidays.

Figure 14:
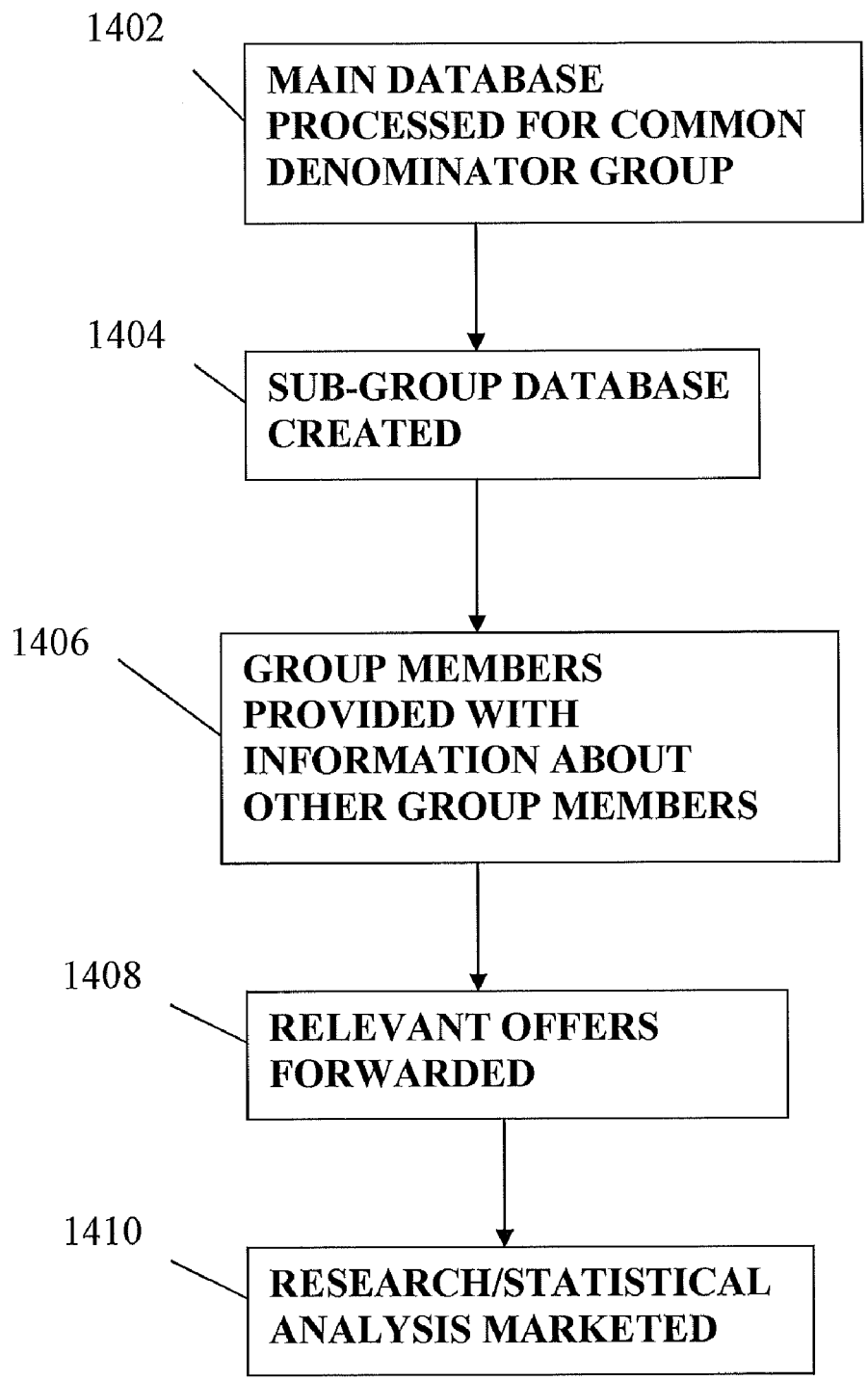
FIG. 14 is a simplified schematic flowchart illustrating a commercial method for using the database of FIG. 1 for marketing/statistical applications in a selected group of individuals.

Reference is now made to FIG. 14, which is a simplified schematic flowchart illustrating a commercial method for using the verified database for marketing/statistical applications in a selected group of individuals.

In a processing step 1402, the main verified database is processed to find all individuals having the following common denominators: e.g., BMI>30 (obese), 18-25 year-old, US Citizens, males, studying in an Ivy League university. In step 1404, a group of individuals having these common denominators is formed in a sub-group database (229 in FIG. 3A). The sub-group members may be informed of the existence of other sub-group members (e.g. via website 223 in FIG. 2; step 1406). For example, some of the group members attending the same university may be provided with communication links to the other group members at that university. In step 1408, some or all of the group members may receive offers for products and/or services relevant to them. For example, all the members in sub-group database 229 attending Harvard may be offered a discounted membership to a local Boston country club.

In an optional market research step 1410, the individuals' response to the sales/services offered in step 1408 may be monitored statistically.

According to some embodiments of the present invention, the identity of the web-surfer (user) is well defined and authenticated, thus, on the basis of this knowledge, a large variety of services and products can be offered to the user, which suits his personal profile.

b) Targeted Advertising

As the user's identity is both authenticated and well-defined, the database of the present invention may be used to define populations for targeted advertising.

For example, a virtual community of 65 year old poker players from Scandinavia may be offered packages including, but not limited to, gamblers anonymous packages, cigarette and cigars, gift playing card sets, individual trips to Las Vegas, membership of a national or regional games/gaming club.

Members of a certain family or virtual community may be offered tourist packages, adapted to that specific family or virtual community. For example American family members having a history in Australia, Britain and Germany may be offered a tour starting in Britain, visiting their ancestor's home towns of Bristol and Bath, followed by a tourist trip of London and Oxford. Thereafter, they are offered to fly to Hamburg to see the graves of their great-great-grandparents, a stop-over in Salzburg to hear Mozart operas, and a flight to Sidney to meet their second cousins. The family members may be East and West coast members who have never met each other and the trip will allow cousins of various degrees to meet for the first time. Additionally, the family members may be offered family and trip memorabilia.

c) Business-to-Relative Advertising and Marketing

The database of the present invention may be used for finding members or relatives of a certain community or family. These members/relatives may be offered certain packages by businesses. Typically, the packages will be matched to the personal profile of the potential buyer and additionally may be matched to the personalized profile of a potential recipient.

For example, the database may comprise data relating to a hundred million of users. Each user has a known birthday. On average, there are thus 300-500,000 users who celebrate their birthday on a specific date. This data may be supplied, for example, to an online marketing website such as Amazon. Amazon may supply by January $20^{th}$ to the hundred closest relatives of each individual having a birthday on Jan. 27, 2007 with a list of gifts suited to the personality and lifestyle of that person. Dan may be such an individual who has his birthday on that date. His family members will be advised of scientific, science-fiction, alternative energy books, suited to his personality Similarly, a list of close friends may be provided with lists of gifts.

The lists may also be matched to the relatives and friends. For example, his daughters may be advised of gifts to match their age and budget. A teenager may be provided with a list of gifts in a $5-10 and $10-30 category. A good friend, employed in the same firm may be offered a list of gifts in the $50-100 category.

The friends and relatives of Dan may also be offered to send him an electronic card or real birthday card.

In another example, members of the Nevada Hang Glider's association may be offered hang gliding equipment, insurance policies, psychological advice, trips to meet with other hang gliders worldwide, energy foods and beverages, literature relating to hang gliding and gliding, and posters, postcards and other hang gliding related material. These offers may be made over the web, or by any other means described with respect to system 200, in FIG. 2.

Family members or community members may be provided with personalized packages which are associated with a local or national holiday, a religious festival or holyday, a national or international historical event, or a community-associated event.

Members of an environmental group in Scotland, for example, may be offered literature relating to oil-spills, Chernobyl fall-out, bird migration and river BOD (Biological oxygen demand) and COD (chemical oxygen demand) impact on trout populations. The members who purchase literature relating to the trout populations may, thereafter, be offered to go on a trout-fishing weekend in the Lake District.

Young parents having babies of the 12-18 month age range (verified from the database) and living in Amsterdam and Munich may be offered a new diaper/nappy suited to that age group.

Members of a virtual community, such as a virtual "ABBA" fan club, may be offered ABBA memorabilia in a targeted auction or online garage sale. For example, a pair of boots worn by Bjorn at the Eurovision Song Contest, in which he sang "Waterloo" may be offered to members of this virtual community.

Similar sales and auctions may be offered to family members. For example, Jeremy Bentham's clothes (currently property of University College London, UK) may be offered for sale to all of his known descendants in an online auction.

Family members or virtual community members may be offered "time out" activities suited to the family or community. For example, a virtual community of actors/actresses may be offered special deals for theatrical shows, musicals, films, DVDs and videos. Additionally, members can be offered to meet each other to perform "My Fair Lady" at the local theatre. Likewise, the local theatre may be provided with a list of suitable candidates to perform a theatrical role. The database can be used to provide candidates who meet the following criteria: a female aged 18-35 who can sing, speak with both an Oxbridge and a Cockney accent in English, as well as being attractive, 1.65-1.73 m, blond and slim.

The database of the present invention may be used to perform numerous analyses of individual types from verified and authenticated data. This data can be used for many different types of applications exemplified by, but not limited to, the examples described herein.

The database of the present invention may be used to perform numerous types of sectorial marketing and advertising, exemplified by, but not limited to, the examples described herein. It should be understood that the information relating to family relatives and community members may be used off-line by commercial establishments as well as on-line.

d) Multi-Level Marketing

The database of the present invention may be used to perform optimized multi-level marketing within a family or community. The knowledge of the lifestyle of the individuals within the family or community may be used to define the better and worse targets for a certain product or service. Thus, for example, all female family members aged 55+ may be offered a "new age anti-aging face cream" using multi-level marketing.

EXAMPLE 3

Statistical Research

The database of the present invention may be used for epidemiological studies, trend studies, consumer studies within a geographic location, population, real or virtual community or family.

Sectorial statistical studies may be performed relating to longevity of a sector or population, disease analysis, consumer analysis.

For example, a market research program can be performed on male 45 year old academics who live on the US West Coast. A tobacco company may wish to know the opinions of members of such a sector relating to a new potent genetically engineered caffeine and nicotine containing tobacco product.

A government may wish to map the number of pension-less pensioners in a district who do not have medical insurance. Again, this sector can be mapped directly from active users as well as from passive users, whose information is obtained from active users.

EXAMPLE 4

Identifying Hostile Persons, Lost Persons, Relatives of Deceased Persons, Possessions of the Deceased Persons From Family Tree Databases The methods and systems for forming family trees described herein are unique in that the family members are authenticated to a very high level of confidence. Thus, users who are not verified over a period of time may become suspects for having provided false information. These users will be identified as "floating branches" which are not attached to any other branch. They will not be granted access to the database as they are not verified.

These unverified individuals may also provide clues as to their true identity by trying to access certain close relatives and/or friends. In some cases, the system of the present invention may be able to provide a geographic location of such a person, which may be used by a family searching for a lost individual, a police, government or legal establishment for finding that person.

Figure 15:
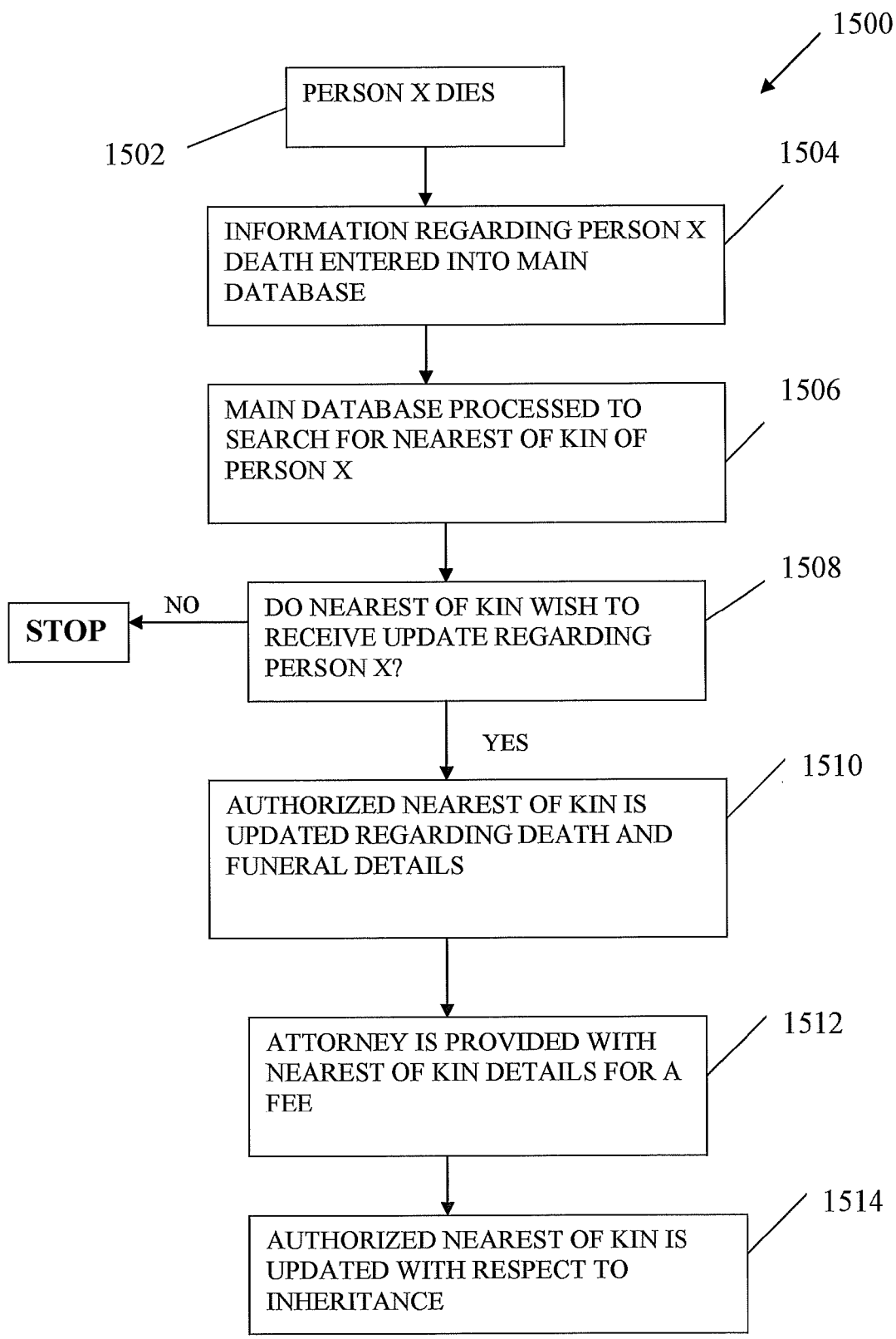
FIG. 15 is a simplified schematic flowchart illustrating a commercial method for using the database of FIG. 1 for a legal application in a selected group of individuals.

Reference is now made to FIG. 15, which is a simplified schematic flowchart 1500 illustrating a commercial method for using the verified database for a legal application in a selected group of individuals.

A person may die or be killed in step 1502. The information pertaining to the deceased may be advertised in the media or may be available in local or national government records.

In a feeding step 1504, an individual may enter the information regarding the deceased into database 227 (FIG. 3A). Alternatively, the information may received electronically.

In searching step 1506, processor 228 is operative to search for nearest of kin/relatives of the deceased in database 227. If some relatives/nearest of kin are found, they are asked in step 1508 if they wish to be updated with respect to the status of the deceased individual. If no, they are not informed.

If yes, the nearest of kin are updated in updating step 1510 with respect to the death of the individual and any funeral arrangements.

In an informing step 1512, the information regarding the nearest of kin can be provided to the attorney of the deceased, for a fee. The attorney can then contact the nearest of kin/relatives and update them in step 1514 with respect to the inheritance of an intestate deceased individual via the standard legal procedures of the specific jurisdiction of the deceased.

There are thousands if not millions of unclaimed bank accounts, pensions, insurance and endowment policies worldwide. The database of present invention can be used to remind individuals of their own accounts, and further to appropriate such accounts to the nearest of kin of a deceased individual.

Disputes pertaining to land ownership, may, at least in part, be solved using the data from the databases of the present invention.

EXAMPLE 5

Family Applications of Family Tree Databases

Users may be informed of new relatives added to their family tree and thus be updated in real time with respect to "newly found relatives".

EXAMPLE 6

Extraction of Data From Family Trees to Create Family Portals

Some embodiments of the present invention are directed to a family portal or family website, in which members of the family, who appear on the family tree are members thereof and have access thereto.

By portal is meant a Web page that serves as a point of entry for surfers of the World Wide Web. It should be noted that most of the popular portals are designed to optimize their compatibility with one or more Web search engines. Many portals also offer value-added services such as e-mail accounts, Web page hosting, or filtered information flow, with the costs of these services being underwritten by advertising.

A family website, according to some embodiments, includes services specific to members of the family, such as, but not limited to, a system for sharing photos, videos, an organizational chart an events calendar, a Roots family record, systems for communication between the family members, such as Messenger or a voice communication system operating over a computer network, e.g. a voice over IP system operation over the Internet.

The information which exists in the tree, such as names of family members and the connections and relationship between them are used as a basis for the formation of the portal. For example, the Johnson family may define the family website's name, authorization of access, development of personal websites for each family member separately, his picture, his birthday, his personal profile which is derived, at least partially, from the data in the family tree.

Similarly, family books and/or online newspapers may be formed from the data in the family tree.

EXAMPLE 7

Methods of Combining Different Forms of Family Information

According to some embodiments of the present invention, information found in family trees in paper form or published in books may be converted by means of standard optical character recognition (OCR) methods known in the art into digital or analog information. In some cases, the paper tree or other paper form may be scanned and saved to disk, prior to performing OCR.

According to some embodiments, the ability of family members to communicate within the portal/website is such that each family member knows what the relationship between him/her and the other people communicating within the portal is. This may be found by reference to the family tree or by being able to access the information via a standard search engine as is known in the art. Furthermore, the family member may have access to one or more of the following: screenshots pertaining to family members, a family calendar, an online family tree, a family database and a corresponding family organizational chart. Each individual may define the family members from whom he wishes to receive information and to whom he wishes to provide information.

An individual or family may appear in one or more portals and in one or more family trees.

A user may be provided, for example, with a calendar of family events via the portal, such as by providing reminders regarding events such as birthdays, the information of which it extracts from the family tree database .

According to some embodiments, an individual is characterized according to his personalized parameters, such as, but not limited to, age, gender, hierarchical location in a family tree or chart, geographical location, nationality and religion. If the individual's personalized parameters meet a certain criterion or various criteria, he may be automatically provided by the system with at least one of: advertisements, sales offers, media items, stories, family-related information or material.

In some cases, the individual receives at least one of: advertisements, sales offers, media items, stories, family-related information or material from another family member. In some cases, the individual will have control of the material which he receives and in some other cases the other family member (sender) will have a degree of control of the material sent to the individual.

EXAMPLE 8

Extraction of Data From a Family Tree to Create Individual Web Pages Therefrom

This invention, according to some embodiments, is directed to methods for automatic generation of a web page by processor for every individual in the family tree by extracting the data pertaining to the individual from the family tree database and transferring it to a web page via LAN/WAN for display at one or more interfaces. The data may include the individual's name, date of birth, names of parents and the like.

EXAMPLE 9

The Chronology- Display Application Showing Family Events in Chronological Sequence A chronological personified time line may be created from the family tree database, in accordance with certain embodiments of the present invention. Data is extracted from at least one of a family tree database, a family tree display and/or from family or individual web pages.

A time line comprises divisions, which may extend over part or all of the screen. Each division signifies a period of time Personalized events are displayed chronologically and are provided with titles in the language of the individual.

Data pertaining to the personalized time line may be extracted from the family tree database, from an online/offline family tree, from national or church records or any other data source known in the art.

1) Family Forum and Chat

Another application of the data found in the family tree database, or from an online/offline family tree, is using the data in a family forum. An individual may send a message to another family member. Processor provides the senders true name to the recipient. Furthermore, his personal details as appearing in the family tree and/or on his personal web page may be automatically provided to the family forum.

Two or more family members may communicate to each other, each one knowing the true identity and degree of relatedness of him to the others. This system allows for "many to many" communication, including electronic communication such as emails and SMSes and voice communication over the internet and over other communication systems known in the art.

2) Family Messenger

A message may be sent from a sender to a recipient and the processor is configured to provide at least one of the sender and recipient with details of the family connection between them. For example, the processor may extract the information from the family tree database, from a family tree (not shown), from a web page and provide the information with the message on a display at one or more of the interfaces.

EXAMPLE 10

Photograph and Portrait Authentication

A portrait, photograph or other image of a person who is known by at least one family member may be identified by the family member and stored in the family tree to database or by the system at an image bank location. Images of one or more unidentified individuals may be fed into system 200 and may be compared by image analysis methods known in the art. Using this methodology a family tree image bank may be compiled. Upon merging of small family trees by methods known in the art, a national or international/world family tree image bank (FTIB) may be formed. The FTIB may be used by local and international police an intelligence services, as well as for, amongst others, genetic, epidemiological, and anthropological studies.

EXAMPLE 11

Personalized Sectorial Searches

A user can perform a search using the database of the present invention to map his relatives aged 30-35, who live in Australia, with the provisos, that the relatives are of the third degree or closer and are active users.

A user may wish to find friends of a certain type or persuasion. He may use the website of the present invention to seek such friends based upon their authenticated identities and characteristics.

A user may be provided with a family tree, a family chart, a family table or any other family display described herein. The user may be the center of the tree or chart and this may assist him in locating family members and understanding the degree of relatedness between himself and the family member(s).

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways.

Those skilled in the art will readily appreciate that various modifications and changes can be applied to the embodiments of the invention as hereinbefore described without departing from its scope, defined in and by the appended claims.

The invention claimed is:

1. A method for using and managing a database, the method comprising:
   providing a verified database of a plurality of identified individuals, the verified database comprising a plurality of individual-identifier data sets (IDSs) and relationship data; and
   processing said verified database in accordance with one or more parameters or conditions selected in accordance with at least one medical application and creating a sub-group database including data records of the individuals from the verified database having said one or more selected parameters or conditions, thereby allowing collection of data comprising one or more selected parameters or conditions and delivery of at least part of the collected data to one or more users and enable to apply data from said verified database to provide personalized medicine service to at least one of said identified individuals;
   wherein said providing of the verified database comprises:
      permitting a plurality of individuals to enter individual-associated data bits (IDBS) into a computerized system, each of the IDBs comprising at least one personal identifier relating to the individual and relationship data comprising data on one or more related individuals and the nature of relationship;
      processing the entered IDBs to generate the IDS, one for each identified individual, being either said individual who has entered the individual-associated data bits or one of the related individuals and construct the verified database comprising IDSs of identified individuals.

2. A method according to claim 1, wherein said processing of the verified database in accordance with said one or more selected parameters or conditions is initiated by a request from a user.

3. A method according to claim 2, wherein said user is the individual whose data is included in the verified database.

4. A method according to claim 1, wherein said processing comprises generating a request to at least some of the individuals whose data is included into the verified database to provide additional data according to said one or more selected parameters or conditions.

5. A method according to claim 4, comprising updating the verified database with the additional data received from at least some of the individuals, and applying said processing to the updated verified database to create the sub-group database.

6. A method according to claim 1, wherein the selected parameters or conditions include at least one parameter or condition selected according to one of the following applications: a commercial application, sectorial and targeted marketing application, a statistical application, an identifying application selected from identifying a hostile person, a lost person, a relationship between a deceased person and living person, a family application.

7. A method according to claim 1, wherein said processing of the verified database comprises creating a medical database of at least some of said identified individuals, said medical database comprising information pertaining to at least one of a disease, a medical condition, a genotype, a phenotype, a family relationship; and a geographic location of at least one of said identified individuals.

8. A method according to claim 1, wherein said at least one medical application is based upon personalized medicine.

9. A method according to claim 1, wherein the processing of the verified database comprises filtering said verified database to create the subgroup of identified individuals.

10. A method according to claim 9, comprising providing at least one of a product and a service to at least one individual of said subgroup.

11. A method according to claim 10, wherein the provision step is responsive to information pertaining to said at least one individual.

12. A method according to claim 1, wherein said processing comprises constructing a family database for each individual.

13. A method according to claim 12, comprising:
   a) constructing at least two IDSs for corresponding at least two identified first individuals;
   b) identifying at least two IDSs having overlapping relationship data including at least one identical identified individual in the corresponding relationship data; and
   c) consolidating the at least two relationship data pieces to construct an expanded relationship data record.

14. A method according to claim 13, comprising constructing an expanded family database that comprises all family databases which are overlapping family databases and comprise data identifying the connection between individual of the expanded family database.

15. A method according to claim 7, comprising combining at least one personal medical record with data from the verified database.

16. A method according to claim 15, comprising providing personalized medical service selected from a personalized treatment service, a personalized prevention service and a personalized prediction service.

17. A computerized system for managing and using a database over a computer network, the system comprising a server system linked to the network and accessible by users via their communication devices connectable to the network, said server system comprising a processor utility, which is associated with a verified database of a plurality of identified individuals comprising a plurality of individual-identifier data sets (IDSs) and relationship data and which is adapted to carry out the following; process said verified database in accordance with one or more parameters or conditions selected according to at least one medical application and create a sub-group database comprising data about at least some of the identified individuals characterized by said one or more selected parameters or conditions, and apply data from said verified database in order to provide a personalized medicine service to at least one of said identified individuals;
configured to carry out the following:
receive a plurality of individual-associated data bits (IDBS) entered by clients, the IDBs comprising personal identifiers and relationship data, the relationship data comprising data on one or more related individuals and the nature of relationship, generate an individual-identifier data set (IDS), one for each identified individual, being either one of the users or one of the related individuals, process all the IDSs and construct a verified database comprising IDSs of identified individuals and their position in a relationship web, and process the information in said verified database according to said at least one selected parameter or condition and create the corresponding sub-group database of at least some of said identified individuals.

18. A system according to claim 17, wherein said processor utility is responsive to a user request to perform said processing of the verified database and creation of the sub-group database.

19. A system according to claim 17, wherein said server system comprises a second processing utility configured to be responsive to a command from the first processing utility to generate a request to at least some of said identified individuals to provide additional data according to said one more parameters and conditions to thereby updating of the sub-group database.

20. A system according to claim 19, wherein said second processing utility is configured for updating the verified database with said additional data.

21. A system according to claim 17, wherein said first processing utility is configured for using said sub-group database for collecting certain information from and/delivering certain information to at least some of the identified individuals of said sub-group database.

22. A system according to claim 17, wherein said sub-group database comprises a medical database comprising information pertaining to at least one of a disease, a medical condition, a genotype, a phenotype, a family relationship; and a geographic location of at least one of said identified individuals.

23. A computerized system for managing and using a database, the system comprising a server system accessible by users via their communication devices connectable to the server system, said server system comprising a processor utility, which is associated with a verified database of a plurality of identified individuals comprising a plurality of individual-identifier data sets (IDSs) and relationship data and which is adapted to carry out the following: process said verified database in accordance with one or more parameters or conditions selected according to at least one medical application and create a sub-group database comprising data about at least some of the identified individuals characterized by said one or more selected parameters or conditions, and apply data from said verified database in order to provide a personalized medicine service to at least one of said identified individuals;
wherein said providing of the verified database comprises:
permitting a plurality of individuals to enter individual-associated data bits (IDBS) into a computerized system, each of the IDBs comprising at least one personal identifier relating to the individual and relationship data comprising data on one or more related individuals and the nature of relationship; processing the entered IDBs to generate the IDS, one for each identified individual, being either said individual who has entered the individual-associated data bits or one of the related individuals and construct the verified database comprising IDSs of identified individuals.

* * * * *